United States Patent [19]

Johnson et al.

[11] 4,035,360

[45] * July 12, 1977

[54] MAGNESIUM SALTS OF 2-DESCARBOXY-2-(TETRAZOL-5-YL)-11-DESOXY-15-SUBSTITUTED-OMEGA-PENTANOPROSTAGLANDINS

[75] Inventors: Michael R. Johnson; Thomas K. Schaaf; Jasjit S. Bindra; Hans-Jurgen E. Hess; James F. Eggler, all of New London, Conn.

[73] Assignee: Pfizer Inc., New York, N.Y.

[ * ] Notice: The portion of the term of this patent subsequent to Jan. 13, 1993, has been disclaimed.

[21] Appl. No.: 642,736

[22] Filed: Dec. 22, 1975

Related U.S. Application Data

[63] Continuation-in-part of Ser. No. 531,675, Dec. 11, 1974, Pat. No. 3,932,389.

[51] Int. Cl.² ............ C07D 257/06; C07D 409/08; C07D 257/04

[52] U.S. Cl. ............ 260/240 R; 260/468 D; 260/308 D

[58] Field of Search ........ 260/240 R, 468 D, 308 D

[56] References Cited

U.S. PATENT DOCUMENTS

| | | | |
|---|---|---|---|
| 3,629,071 | 12/1971 | Sekhar | 260/468 D |
| 3,839,409 | 10/1974 | Bergstrom | 260/468 D |
| 3,853,854 | 12/1974 | Weinshenker | 260/468 D X |
| 3,932,389 | 1/1976 | Johnson et al. | 260/240 R |

*Primary Examiner*—Allen B. Curtis
*Attorney, Agent, or Firm*—Connolly and Hutz

[57] ABSTRACT

The magnesium salts of 2-descarboxy-2-(tetrazol-5-yl)-11-desoxy-15-substituted-ω-pentanorprostaglandins are disclosed. The novel prostaglandin salt of this invention have been found to have activity profiles comparable to the parent prostaglandins, but exhibit a greater tissue specificity of action and are further valuable because they are crystalline and thus may be easily isolated, purified and compounded into medicaments.

32 Claims, No Drawings

MAGNESIUM SALTS OF 2-DESCARBOXY-2-(TETRAZOL-5-YL)-11-DESOXY-15-SUBSTITUTED-OMEGA-PENTANO-PROSTAGLANDINS

CROSS REFERENCE TO RELATED APPLICATIONS

This application is a Continuation-In-Part of our co-pending application, Ser. No. 531,675, filed Dec. 11, 1974, now U.S. Pat. No. 3,932,389.

BACKGROUND OF THE INVENTION

This invention relates to certain novel analogs of the naturally occurring prostaglandins. In particular, it relates to novel magnesium salts of 2-descarboxy-2-(tetrazol-5-yl)-15-substituted-ω-pentanorprostaglandins and various novel intermediates useful in their preparation.

The prostaglandins are C-20 unsaturated fatty acids which exhibit diverse physiological effects. For instance, the prostaglandins of the E and A series are potent vasodilators (Bergstrom, et al., Acta Physiol. Scand. 64:332–33, 1965 and Bergstrom, et al., *Life Sci.* 6:449–455, 1967) and lower systemic arterial blood pressure (vasodepression) on intravenous administration (Weeks and King, *Federation Proc.* 23:327, 1964; Bergstrom, et al., 1965, op. cit.; Carlson, et al., *Acta Med. Scand.* 183:423–430, 1968; and Carlson et al., *Acta Physiol. Scand.* 75:161–169, 1969). Another well known physiological action for PGE₁ and PGE₂ is as a bronchodilator (Cuthbert, *Brit. Med. J.* 4:723–726, 1969).

Still another important physiological role for the natural prostaglandins is in connection with the reproductive cycle. PGE₂ is known to possess the utility to induce labor (Karim, et al., *J. Obstet. Gynaec. Brit. Cwlth.* 77:200–210, 1970), to induce therapeutic abortion (Bygdeman, et al., *Contraception*, 4, 293 (1971) and to be useful for control of fertility (Karim, *Contraception*, 3, 173 (1971)). Patents have been obtained for several prostaglandins of the E and F series as inducers of labor in mammals (Belgian Pat. No. 754,158 and West German Pat. No. 2,034,641), and on PGE₁, F₂ and F₃ for control of the reproductive cycle (South African Patent 69/6089. It has been shown that luteolysis can take place as a result of administration of PGE$_{2\alpha}$ [Labhsetwar, Nature, 230, 528 (1971)] and hence prostaglandins have utility for fertility control by a process in which smooth muscle stimulation is not necessary.

Still other known physiological activities for PGE₁ are in the inhibition of gastric acid secretion (Shaw and Ramwell, In: *Worchester Symp. on Prostaglandins*, New York, Wiley, 1968, p. 55–64) and also of platelet aggregation Emmons, et al., *Brit. Med. J.* 2:468–472, 1967).

It is now known that such physiological effects will be produced in vivo for only a short period, following the administration of prostaglandin. Evidence indicates that the reason for this rapid cessation of activity is that the natural prostaglandins are quickly and efficiently metabolically deactivated by β-oxidation of the carboxylic acid side-chain and by oxidation of the 15α-hydroxy group (Anggard, et al., Acta. Physiol. Scand. 81, 396 (1971) and references cited therein). It has been shown that placing a 15-alkyl group in the prostaglandins has the effect of increasing the duration action possibly by preventing the oxidation of the C15-hydroxyl [Yankee and Bundy, JACS 94, 3651 (1972)], Kirton and Forbes, *Prostaglandins*, 1, 319 (1972).

It was, of course, considered desirable to create analogs of the prostaglandins which would have physiological activities equivalent to the natural compounds, but in which the selectively of action and the duration of the activity would be increased. Increased selectivity of action would be expected to alleviate the severe side effects, particularly gastrointestinal side effects frequently observed following systemic administration of the natural prostaglandins (*Lancet*, 536, 1971). A further goal was to produce compounds having the above properties which would be crystalline so that they ready isolation, purification and formulation into medicaments could be achieved.

SUMMARY OF THE INVENTION

These needs are met by the magnesium salts of the 2-descarboxy-2-[tetrazol-5-yl] 11-desoxy-ω-pentanoprostaglandins and their C₁₅ epimers having at the 15-position a hydroxyl or keto group and one substituent of the formula:

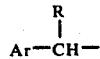

Wherein Ar is α- or β-thienyl; 5-phenyl-α- or β-thienyl; 5-lower alkyl-α- or β-thienyl; α- or β-naphthyl; tropyl, phenyl; 3,4-dimethoxyphenyl; 3,4-methylenedioxyphenyl; 3,4-dichlorophenyl; 3,5-dimethylphenyl; and monosubstituted phenyl wherein said substituent is bromo, chloro, fluoro, trifluoromethyl, phenyl, lower alkyl, or lower alkoxy; and R is hydrogen or methyl and the pharmaceutically acceptable salts thereof. Preferred compounds of this invention are the magnesium salts of 15-substituted -2-descarboxy-2-(tetrazol-5-yl)-11-desoxy-ω-pentanorprostaglandins of the E and F series, their C₁₅ epimers, and 15 keto derivatives.

Such preferred salts are the magnesium salts of compounds represented by the formula:

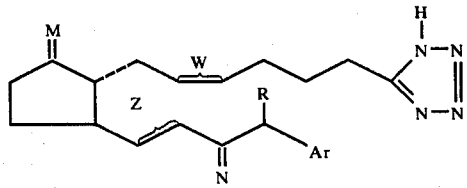

wherein

Ar is α- or β-thienyl; 5-phenyl-α- or β-thienyl; 5-lower alkyl-α- or β-thienyl; α-or β-naphthyl; tropyl; phenyl; 3,5-dimethylphenyl; 3,4-dimethoxyphenyl 3,4-methylenedioxyphenyl; 3,4-dichlorophenyl; and monosubstituted phenyl wherein said substituent is bromo, chloro, fluoro, trifluoromethyl, phenyl, lower alkyl, or lower alkoxy; R is hydrogen or methyl;

and wherein M and N are each

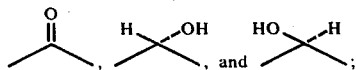

W is a single bond or cis double bond; and
Z is a single bond or trans double bond.

In addition to the magnesium salts of the above prostaglandins wherein said prostaglandin is PGE$_2$, PGE$_1$, PGF$_{2\alpha}$, PGF$_{2\beta}$, PGF$_{1\alpha}$, PGF$_{1\beta}$, PGE$_0$, PGF$_{0\alpha}$, PGF$_{0\beta}$, 13,14-dihydro PGE$_2$, 13,14-dihydro PGF$_{2\alpha}$ and 13,14-dihydro PGF$_2\beta$, and their C$_{15}$ epimers having at the 15-position a hydroxy or keto group and one substituent of the formula

wherein Ar is α- or β-thienyl; 5-phenyl-α- or β-thienyl; 5-lower alkyl-α- or β-thienyl; α- or β-naphthyl; tropyl, phenyl; 3,5-dimethyl phenyl; 3,4-dimethoxyphenyl; 3,4-methylenedioxyphenyl; 3,4-dichlorophenyl; and monosubstituted phenyl wherein said substituent is bromo, chloro, fluoro, trifluoromethyl, phenyl, lower alkyl, or lower alkoxy; and R is hydrogen or methyl;

An especially preferred series of novel salts is the magnesium salts of compounds represented by the formula:

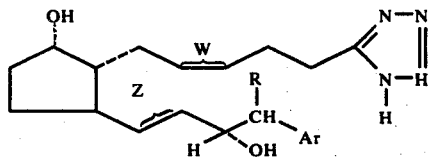

and its C$_{15}$ epimer

Another especially preferred series of novel salts is the magnesium salts of compounds represented by the formula:

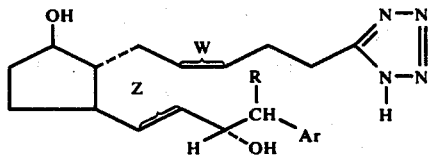

and its C$_{15}$ epimer

Still other especially preferred novel salts are magnesium salts of compounds represented by the formula:

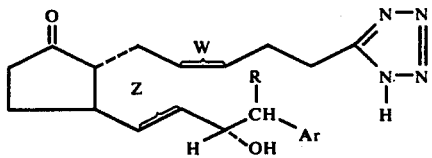

and its C$_{15}$ epimer wherein R, Ar, W and Z as defined above.

Another especially preferred series of novel salts is magnesium salts of compounds represented by the formula:

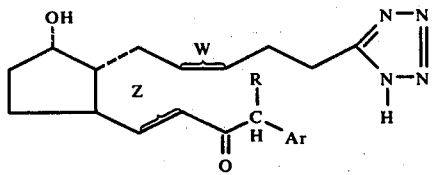

Another especially preferred series of novel salts is the magnesium salts of compounds represented by the formula:

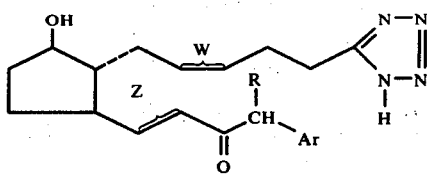

Still other especially preferred novel compounds are magnesium salts of compounds represented by the formula:

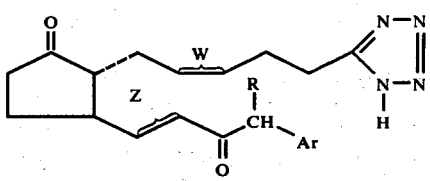

wherein R, Ar, W and Z are as defined above.

Especially preferred are the magnesium salts of the following compounds:

15-keto-11-deshydroxy-16-(m-tolyl)-2-descarboxy-2-(tetrazol-5-yl)-Ωtetranorprostaglandin E$_2$, 15-keto-11-deshydroxy-16-phenyl-2-tetrazol-5-yl)-Ω-tetranorprostaglandin E$_2$, 15keto-11-deshydroxy-16phenyl-2descarboxy-2-(tetrazol-5-yl)-Ωtetranorprostaglandin E$_0$, 15keto-11-deshydroxy-16-phenyl-2-descarboxy2-(tetrazol-5-yl)-ω-tetranorprostaglandin E$_1$, 15-keto-11-deshydroxy-16-(m-tolyl)-2-descarboxy-2-(tetrazol-5-yl)-13,14-dihydro-ω-tetranorprostaglandin E$_2$, 15-keto-11-deshydroxy-16-(m-tolyl)-2-descarboxy-2-(tetrazol-5-yl)-ω-tetranorprostaglandin F$_{2\alpha}$, 15-keto-11-deshydroxy-16-(m-tolyl)-2-descarboxy-2-(tetrazol-5-yl)-13,14-dihydro-ω-tetranorprostaglandin F$_{2\alpha}$, 11-deshydroxy-16-(5-phenyl-α-thienyl)-2-descarboxy-2-(tetrazol-5-yl)-ω-tetranorprostaglandin E$_2$, 11-deshydroxy-16-((+-methyl-16phenyl-2-descarboxy-2-(tetrazol-5-yl)-Ω-tetranorprostaglandin E$_2$, 11-deshydroxy-16-((+)-methyl)-16-phenyl-2-descarboxy-2-(tetrazol-5-yl)-ω-tetranorprostanglandin E$_o$, (±)-11-deshydroxy-16-(β-naphthyl)-2-descarboxy-2-(tetrazol-5-yl)-ω-tetranorprostaglandin E$_2$, (±)-15-epi-11-deshydroxy-16-(β-naphthyl)-2-descarboxy-2-(tetrazol-5-yl)-ω-tetranorprostaglandin E$_2$, 11-deshydroxy-16-phenyl-2-descarboxy-2-(tetrazol-5-yl)-ω-tetranorprostaglandin E$_o$, and 11-deshydroxy-16-(m-tolyl)-2-descarboxy-2-(tetrazol-5-yl)-ω-tetranorprostaglandin E$_2$.

DETAILED DESCRIPTION OF THE INVENTION

As shown in Scheme A, the first step (1 → 2) is a condensation between the known aldehyde 1 (Corey and Ravidranathan, *Tetrahedron Lett.*, 1971, 4753 with an appropriate 3-keto phosphonate to produce enone 2. The keto phosphonate is usually produced by condensation of the appropriate carboxylic acid ester with a dialkyl methyl phosphonate. Typically the desired methyl ester is condensed with dimethyl methyl phosphonate.

Enone 2 is then reduced to enol 3 with zinc borohydride or a hindred alkyl borohydride such as lithium triethylborohydride. This reduction produces a mixture of epimers both of which may be used as substrates for further reactions. The 3 is used to produce prostaglandin analogs having an α-hydroxyl at $C_{15}$. The epimer of 3 is used to produce prostaglandin analogs having a β-hydroxyl at $C_{15}$. In addition, the mixture of $C_{15}$ epimers may be used to produce 15-keto prostaglandin analogs. The epimers produced in the hydride reduction can be separated by column preparative thin layer or preparative high pressure liquid chromatography. In the reduction reaction ethers such as tetrahydrofuran or 1,2-dimethoxyethane are usually employed as solvents.

Enone 2 may be reduced catalytically with hydrogen to ketone 6, a suitable starting material for the preparation of 13,14-dihydro prostaglandin tetrazol analogs of the present invention. This reduction may be achieved with either a homogenous catalyst such as tris-triphenylphosphinerhodiumchloride or with a heterogenous catalyst system such as platinum, palladium or rhodium. The stage at which the reduction is carried out is not critical as will be seen below.

Scheme A

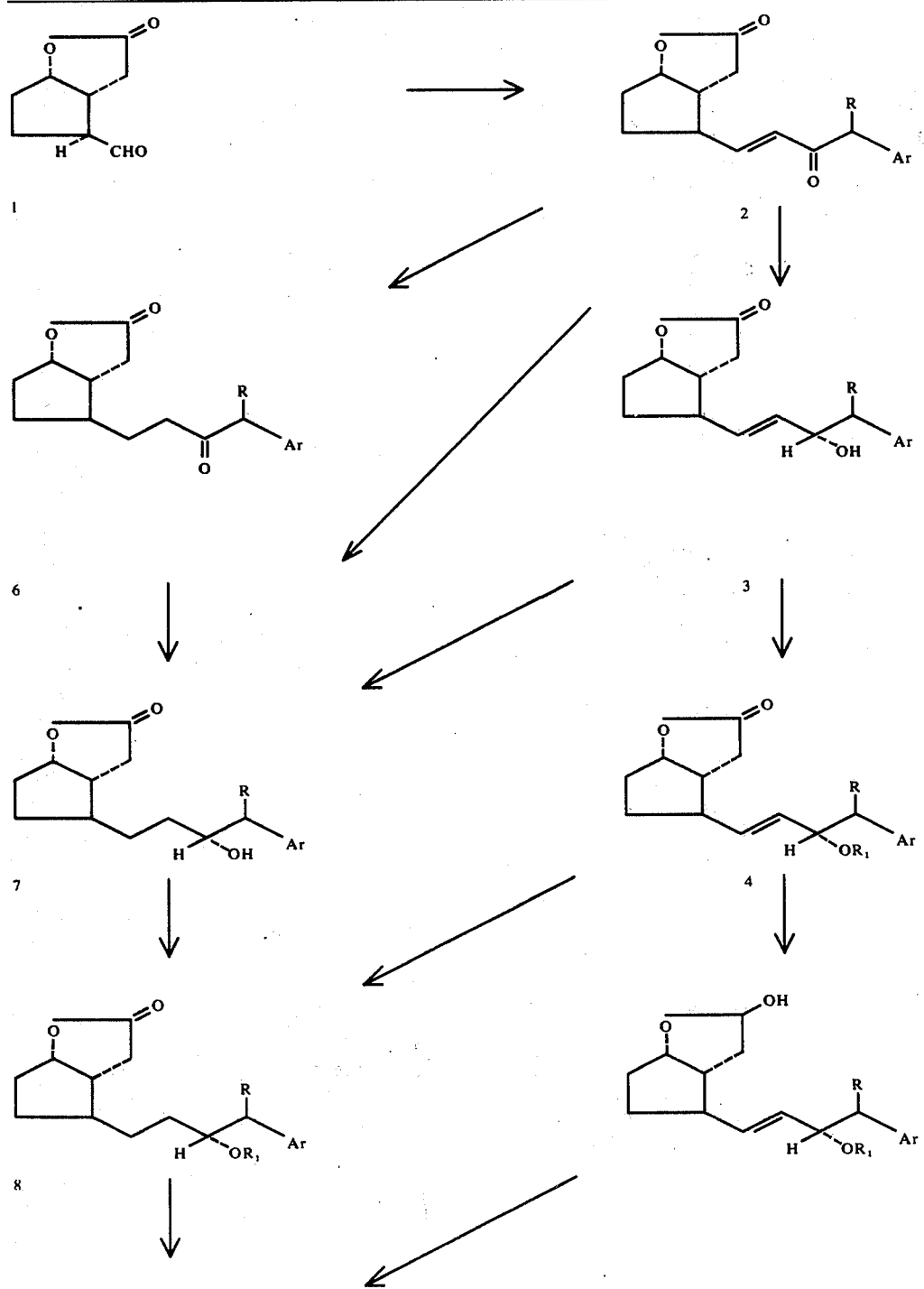

Scheme A-continued

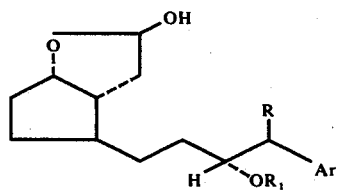

9

Enone 2 may also be reduced with borohydride ion to produce alcohol 7 in a single step or alternatively, enol 3 may be catalytically reduced to produce alcohol 7 using conditions described above.

(3 → 4) involves the protection of the free hydroxyl group with an acid labile protecting group. Any sufficiently acid labile group is satisfactory, however, the most usual ones are tetrahydropyranyl or dimethyl-tert-butylsilyl which can be incorporated in molecule by treatment with dihydropyran and an acid catalyst, usually p-toluenesulfonic acid, in an anhydrous medium or dimethyl-tert-butylsilyl chloride and imidazole, respectively.

(4 → 5) is a reduction of the lactone 4 to hemiacetal 5 using a suitable reducing agent such as diisobutyl aluminum hydride in an inert solvent. Low reaction temperatures are preferred and −60° to −70° C. are usual. However, higher temperatures may be employed if over reduction does not occur. 5 is then purified if desired by column chromatography. As indicated in Scheme A, compounds 4 and 5 may be catalytically reduced to 8 and 9 respectively, by the procedure outlined above.

The conversion of (6 → 9) follows that already outlined by the conversion of (2 → 5).

The remainder of the synthesis of the two- series prostaglandin analogs of this invention is outlined in Scheme B. (5 → 10) is a Wittig condensation in which hemiacetal 5 is reacted with 4-(tetrazol-5-yl)butyltriphenylphosphonium bromide (22) in dimethyl sulfoxide in the presence of sodium methylsulfinyl methide.

Scheme B

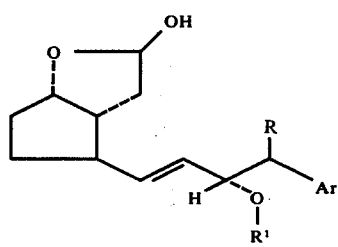

5

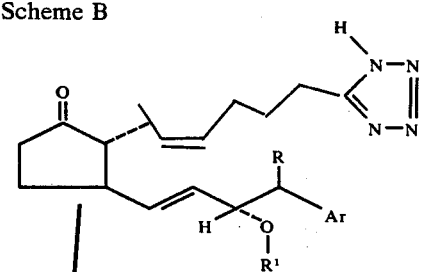

12

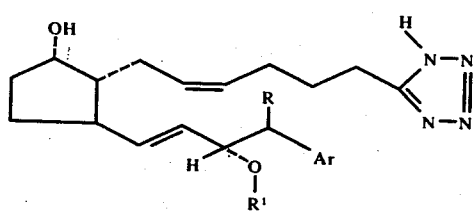

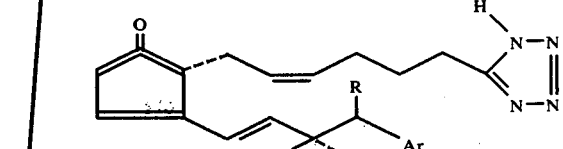

Scheme B—continued

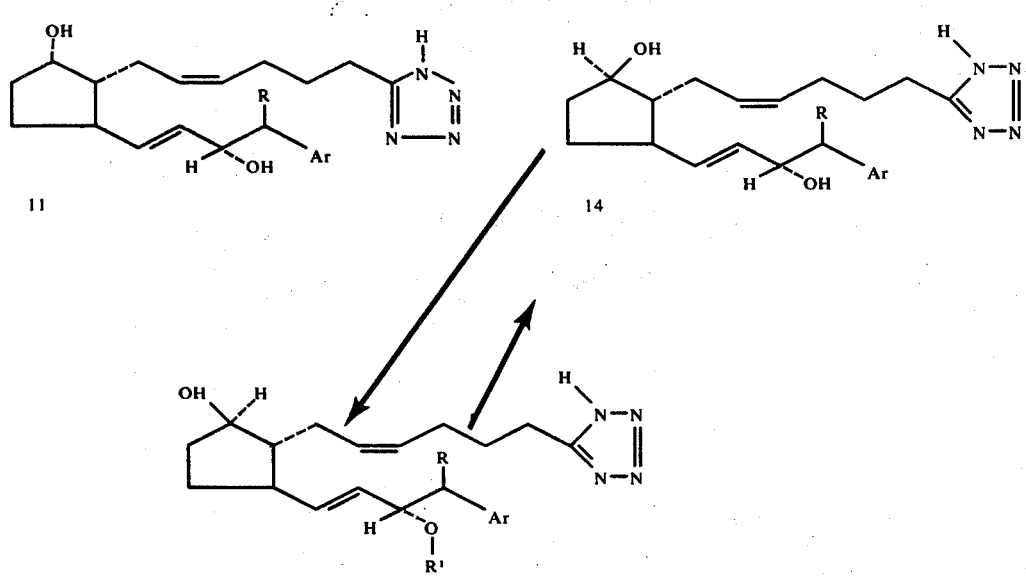

10 is then purified as above. The conversion of 10 → 11 is an acid catalyzed hydrolysis of protecting group. Any acid may be used which does not cause destruction of the molecule in the course of the removal of the protecting group, however this is accomplished most often by the use of 65% aqueous acetic acid. Alternatively, the dimethyl-tert-butylsilyl protecting group may be removed by the action of tetraalkylammonium fluoride in a solvent such as tetrahydrofuran. The product is purified as above.

11 is an 11-desoxy 15-substituted-ω-pentanorprostaglandin of the $F_{2\alpha}$ series. The prostaglandin tetrazol analogs of the $E_2$ series of this invention (13) are prepared from intermediate 10 which may be oxidized by any reagent capable of oxidizing hydroxyl groups which does not attack double bonds. However, the Jones reagent is usually preferred. The product is purified as above to produce intermediate 12. Intermediate 12 may be converted into the prostaglandin analogs of the $E_2$ series (13) of this invention in the same manner as described for (10 → 11). Furthermore, intermediate 12 may be reduced with sodium borohydride to a mixture of intermediate 15 and its $C_9$ epimer which are separable by column, preparative thin layer, or preparative high pressure liquid chromatography and which can be converted into prostaglandin tetrazol analogs of the $F_{2\alpha}$ and $F_{2\beta}$ series of this invention by the methods given for (10 → 11). Alternatively, compound 13 may be reduced with sodium borohydride to provide the $F_{2\alpha}$ and $F_{2\beta}$ prostaglandin tetrazol analogs of this invention directly. This epimeric mixture may be separated as described above for 15 to provide pure $PGF_{2\alpha}$ and $PGF_{2\beta}$.

The various reduced tetrazol prostaglandin analogs of this invention, that is, prostaglandins of the one, zero and 13,14-dihydro two series are produced as shown on Scheme C. Intermediate 6 may be converted to 19 by the steps already outlined for the conversion of (2 → 10). 19 may then be converted to 20 by the steps discussed above for the conversion 10 → 15. 20 may be catalytically reduced to produce 18 ($R_1$ THP or $(CH_3)_2Si\ C(CH_3)_3$) which is the precursor for the prostaglandin tetrazol analogs of the zero series of this invention by the steps previously outlined (16 → 17) is a selective catalytic hydrogenation of the 5-6 cis double bond at low temperature using catalysts such as those described above. Especially preferred for this reduction is the use of palladium on carbon as a catalyst and a reaction temperature of −20° C. 17 ($R_1$ THP or $(CH_3)_2\ Si\ C(CH_3)_3$) is not only a precursor for the prostaglandin tetrazol analogs of the one series of this invention but also for the zero series since 17 may be reduced to 18 reducing the methods described for (4 → 8). Similarly, 16 may be reduced to 18 by the same procedure. The removal of the protecting groups is carried out as previously described and 17, 18, 19, and 20 wherein $R_1$ THP or $(CH_3)_2\ Si\ C(CH_3)_3$ may be deprotected in this way to produce tetrazol prostaglandins of the one, zero, and "13,14-dihydro two" series of this invention. The production of prostaglandins of the E and F series wherein said prostaglandin of the zero, one, or 13,14-dihydro two series from 16, 17, 18, 19 and 20 follows that previously described for the conversion of 10 → 11, 12, 13, 14 and 15.

Scheme C

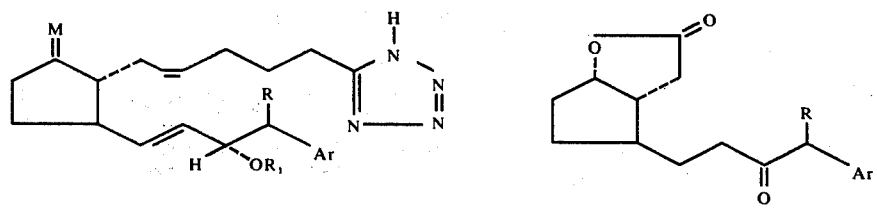

Scheme C-continued

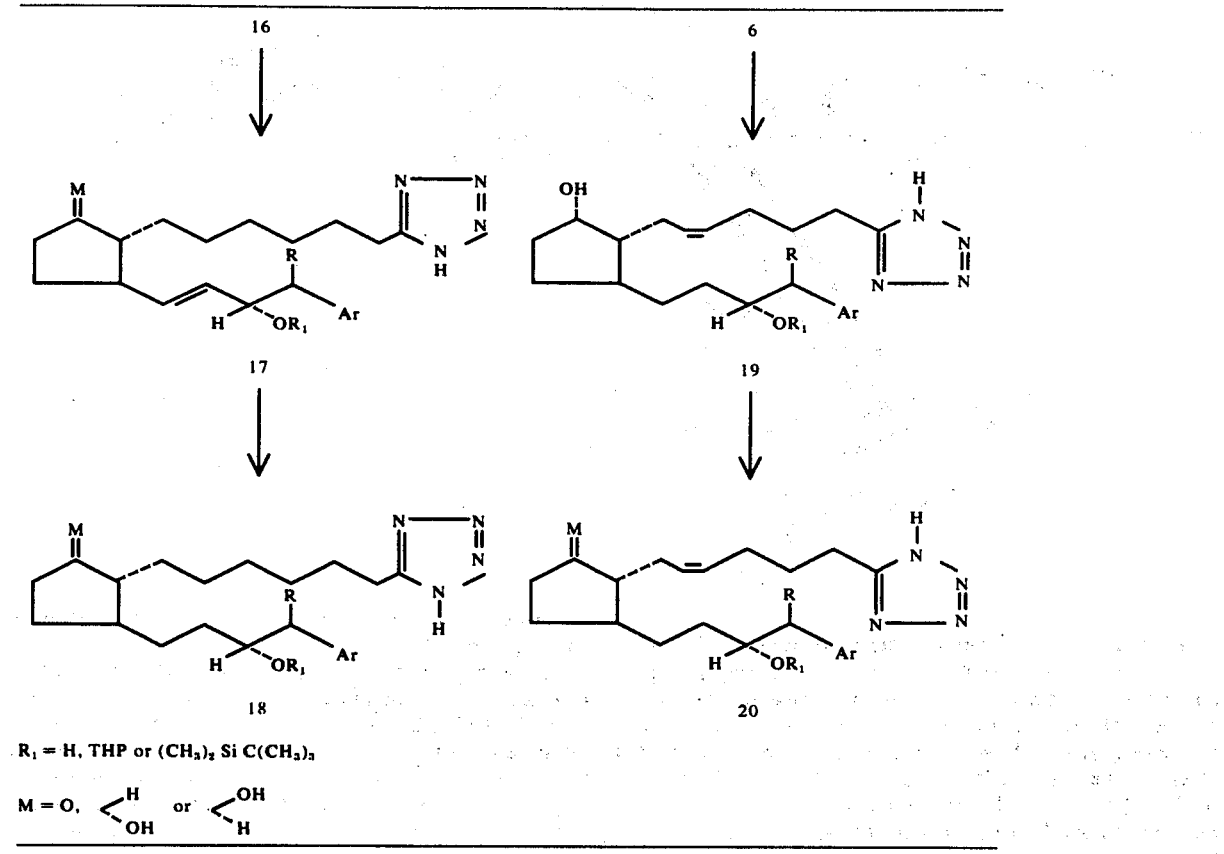

$R_1$ = H, THP or $(CH_3)_2 Si C(CH_3)_3$

M = O, $\overset{H}{\underset{OH}{<}}$ or $\overset{OH}{\underset{H}{<}}$

Furthermore, the 15-substituted-ω-pentanorprostaglandin tetrazol analogs of the $E_1$, $F_{1\beta}$ and $F_{1\alpha}$ series may be obtained directly from the corresponding prostaglandin analog of the "2-series", by first protecting the hydroxyl by introducing dimethyl isopropyl silyl groups reducing selectively the cis double bond, and removing the protecting group.

The reduction is usually accomplished as discussed above for 16 → 17 and removal of the protecting group is accomplished by contacting the reduced protected compound with 3:1 acetic acid: water for 10 minutes or until reaction is substantially complete.

2-descarboxy-2-(tetrazol-5-yl)-11-desoxy-15-substituted-ω-pentanorprostaglandin analogs of the one series may be prepared by the alternate synthesis summarized in Scheme D. For the first step in the preparation of the above named prostaglandin analogs, the hemiacetal 2-[5α-hydroxy-2β-benzyloxymethylcyclopent-1α-yl]-acetaldehyde, γ-hemiacetal is caused to react with the disodium salt of 4-(tetrazol-5-yl)butyltriphenylphosphonium bromide (22) as described above for 5 → 10. This tetrazol-containing intermediate may be converted by procedures described in detail in the appended examples as summarized below.

As shown in Scheme D, hemiacetal 21 is caused to react with the reagent 22 to produce 23.

Scheme D

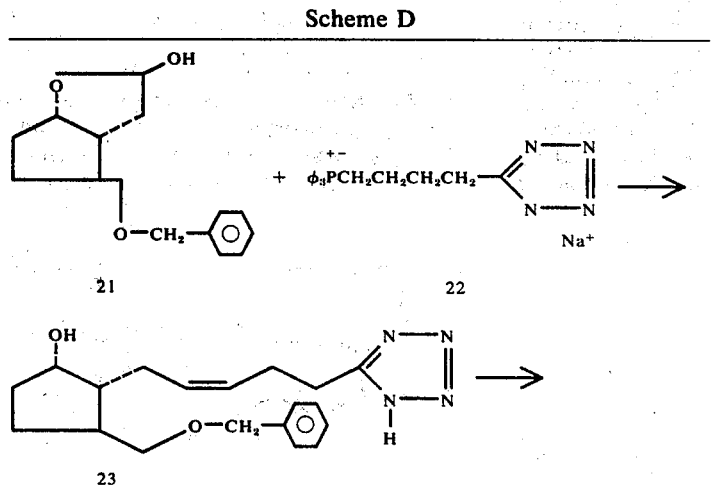

Scheme D-continued

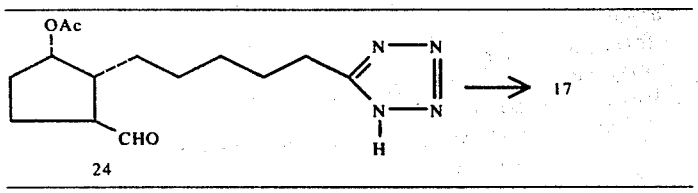

23 → 24 involves acylation of 23 with acetic anhydride and pyridine to form an acetate intermediate. Other blocking groups may be used provided the group is stable to hydrogenation and mild acid hydrolysis. Such groups include alkanoyl of from 2 to 9 carbons, phenalkanoyl of up to 10 carbons, benzoyl, toloyl, p-phenyl benzoyl or α- or β-naphthoyl. The protected benzyl ether upon reduction with hydrogen and palladium on carbon in an appropriate solvent containing a suitable acid catalyst, ethanol and acetic acid or ethyl acetate and hydrochloric acid being especially preferred affords a hydroxy compound oxidation of which with Collins' reagent yields aldehyde 24.

24 → 17 involves treatment of 24 with the sodium salt of the appropriate 3-ketophosphonate under conditions described for 1 → 2, to form an enone reduction of which with a hindred alkyl borohydride such as lithium triethylborohydride or zinc borohydride forms an enol. The hydroxyl group is then protected by treatment with dihydropyran to form a tetrahydropyranyl ether. Other protecting groups may be employed provided they stable to mild basic hydrolysis and easily removable by mild acid hydrolysis. Such groups include tetrahydrofuryl, or dimethyl-t-butyl silyl. This protected compound is then contacted with aqueous sodium hydroxide to yield 17. The conversion of 17 to the 2-descarboxy-2-(tetrazol-5-yl)-11-desoxy-15-substituted-ω-pentanorprostaglandins of the one series of this invention follows the procedure outlined above.

Scheme E

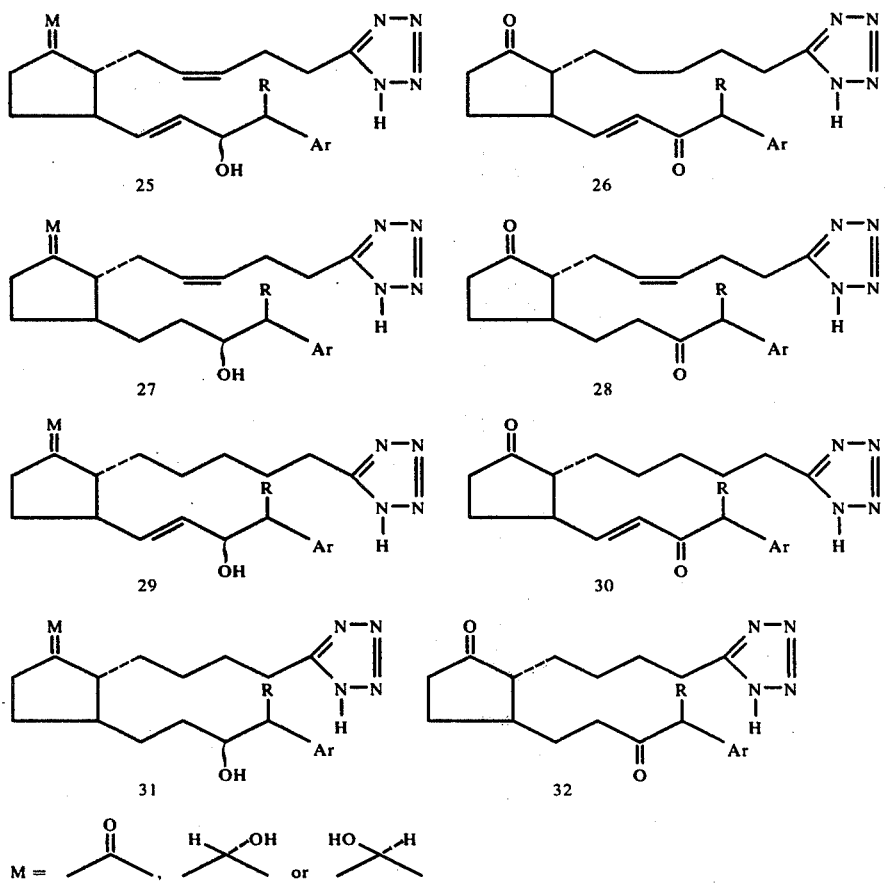

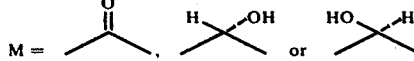

2-Descarboxy-2-(tetrazol-5-yl)-11-desoxy-15-keto-15-substituted-ω-pentanorprostaglandins E of this invention may be prepared as summarized in Scheme E. 25 → 26 involves oxidation of the alcohol moieties of 25. Any reagent capable of oxidizing hydroxyl groups wich does not attack double bonds may be used, however, the Jones' reagent is usually preferred. The 15-keto-prostaglandin E analogs of this invention of the 13,14-dihydro two-, one-, and zero- series may be prepared from compounds 27, 29 and 31 as described for 25 → 26 above.

Scheme F summarizes the preparation of the 2-descarboxy-2-(tetrazol-5-yl)-11-desoxy-15-keto-15- substituted-ω-pentanorprostaglandin $F_\alpha$ and $F_\beta$ analogs of this invention. 33 → 34 involves acylation of 33 with acetic anhydride and pyridine to form an acetate intermediate. Other blocking groups may be used provided the group is stable to mild acid hydrolysis. Such groups include alkanoyl of from 2 to 9 carbons, phenalkanoyl of up to 10 carbons, benzoyl, tolyl, p-phenylbenzoyl, or α- or β-naphthoyl. The protecting group at $C_{15}$ is then removed as described above to provide a second intermediate. The next step involves oxidation of the $C_{15}$ alcohol moiety to provide a third intermediate. Any reagent capable of oxidizing hydroxyl groups which does not attack double bonds may be used, however, the Jones' reagent is usually preferred. The last step in this sequence involves transesterification of the protecting group at $C_9$.

of all 15-keto compounds of the present invention; 15β, 15α, or an epimeric mixture will afford all the same 15-keto analog.

In the foregoing procedures, where purification by column chromatography is desired, appropriate chromatographic supports include neutral alumina and silica gel and 60–200 mesh silica gel is generally preferred. The chromatography is suitably conducted in reaction-inert solvent such as ether, ethyl acetate, benzene, chloroform, methylene chloride, cyclohexane and n-hexane, as further illustrated in the appended examples. Where purification by high pressure liquid chromatography is desired, appropriate supports include 'Corasil,' 'Porasil,' and 'Lichrosorb' with inert solvents such as ether, chloroform, methylenechloride, cyclohexane and n-hexane being employed.

Scheme F

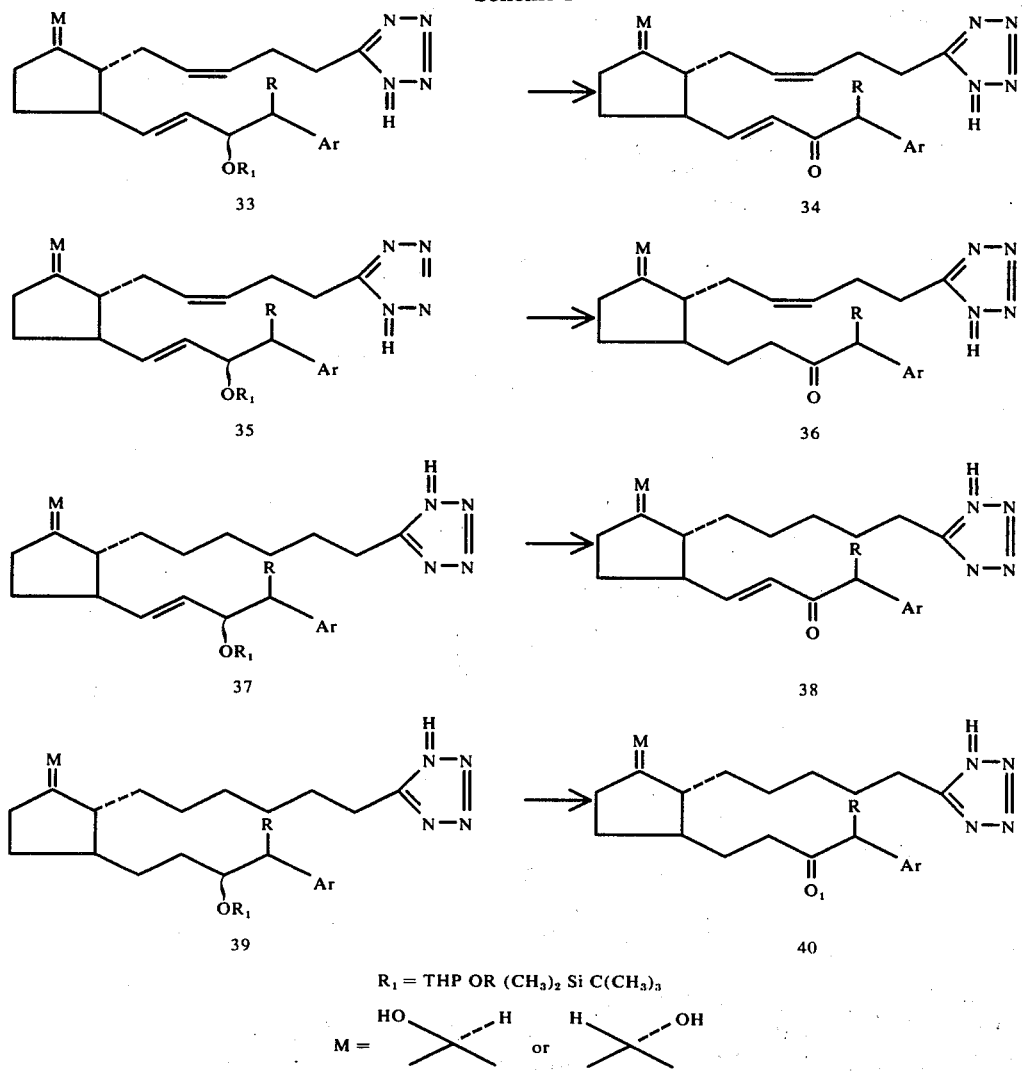

This is usually done by treatment with anhydrous potassium carbonate in an alcoholic solvent such as methanol, which affords the 15-keto $F_{2\alpha}$ or $F_{2\beta}$ analogs of this invention. The 15-keto-prostaglandin $F_\alpha$ or $F_\beta$ analogs of the present invention of the 13,14-dihydro two-, one-, and zero- series may be prepared from compounds 35, 37, and 39 as described for 33 → 34. It should be noted that the stereochemistry of the hydroxyl group at $C_{15}$ is unimportant for the preparation The magnesium salts of the present invention are prepared from the prostaglandin analog from wich they are derived in the following manner: The prostaglandin tetrazol is dissolved in a reaction inert solvent and contacted with magnesium methoxide in methanol at a reaction temperature of −78° C. until reaction is complete (typically 5 minutes) and the reaction mixture is allowed to warm to room temperature and the volatile components of the mixture removed in vacuo. Trituration of the resulting solid with ether gives the desired magnesium salt as a white solid.

It will be seen that the foregoing formulae depict optically active compounds. Although only one optical antipode is depicted it is intended that both optical antipodes (i.e. ent and nat) be embraced by the foregoing formulae herein and in the appended claims. It will be clear, in addition, that the corresponding racemates will exhibit valuable biological activity and it is also intended that such racemates also be embraced by the foregoing formulae herein and in the appended claims. The racemic mixtures are readily prepared by the same methods employed herein to synthesize the optically active species, by mere substitution of corresponding racemic precursors in place of optically active (i.e. end and nat) starting materials. Furthermore, in the foregoing formulae wherein R is methyl an addition chiral center is created. It is intended tha both R and S (+ and −), as well as, racemic forms at this center be embraced by the foregoing formulae herein and in the appended claims.

In numerous in vivo and in vitro tests we have demonstrated that the new magnesium salts of the prostaglandin analogs of the present invention possess physiological activities of greater selectivity, potency, and duration of action to those exhibited by the natural prostaglandins (see above). These tests include, among others, a test for effect on isolated smooth muscle from guinea pig uterus, inhibition of histamine-induced bronchospasm in the guinea pig, effect on dog blood pressure, inhibition of stress-induced ulceration in the rat, diarrheal effect in the mouse, and inhibition of stimulated gastric acid secretion in rats and dogs.

The physiological responses observed in these tests are useful in determining the utility of the test substance for the treatment of various natural and pathological conditions. Such determined utilities include: vasodilator activity, antihypertensive activity, bronchodilator activity, antifertility activity and antiulcer activity.

The novel magnesium salts of 2-descarboxy-2-(tetrazol-5-yl)-11-desoxy-15-substituted-ω-pentanorprostaglandins of this invention possess highly selective activity profiles compared with the corresponding naturally occurring prostaglandins and, in many cases, exhibit a longer duration of action. The novel prostaglandin analogs of this invention possess useful vasodilator activity. A prime example of the therapeutic important of these prostaglandin analogs is the efficacy of the magnesium salts of 2-descarboxy-2-(tetrazol-5-yl)-11-desoxy-16-phenyl-ω-tetranorprostaglandin Eo and 2-descarboxy-2-(tetrazol-5-yl)-11-desoxy-15-((+)-1-phenyleth-1-yl)-ω-pentanorprostaglandin $E_2$ which exhibits hypotensive activity of greatly enhanced potency and duration as compared with $PGE_2$ itself. At the same time, the smooth muscle stimulating activity is markedly depressed in comparison with $PGE_2$. In a simmilar manner, other E and Fβ analogs of this invention exhibit desirable hypotensive activity. The compounds of this invention are especially desirable not only because of their therapeutic activity but also because their high crystallinity allows easy purification and ease of formulation into medicaments.

In addition, the magnesium salts of 2-descarboxy-2-(tetrazol-5-yl)-11-desoxy-16-phenyl-ω-tetranorprostaglandin $E_2$ and 2-descarboxy-2-(tetrazol-5-yl)-11-desoxy-16-(5-phenyl-α-thienyl)-ω-tetranorprostaglandin $E_2$ exhibit high bronchodilator activity with reduced non-vascular smooth muscle activity. In similar fashion, other magnesium salts of 2-descarboxy-2-(tetrazol-5-yl)-11-desoxy-15-substituted-ω-pentanorprostaglandin $E_1$ and $E_2$ analogs of the present invention display desirable bronchodilator activity.

Another outstanding example of the therapeutic importance of these protstaglandin analogs is the potent, selective antiulcer and antisecretory activity displayed by the magnesium salts of 2-descarboxy-2-(tetrazol-5-yl)-11-desoxy-16-(β-naphthyl)-ω-tetranor $PGE_2$ and 2-descarboxy-2-(tetrazol-5-yl)-11-desoxy-15-keto-16-(m-tolyl)-ω-tetranor $PGE_2$. Similarly, other magnesium salts of PGE and 15-keto analogs of this invention possess these desirable gastrointestinal effects.

The esters of the prostaglandin analogs of this invention which are acylated at $C_9$ and/or $C_{15}$ are readily prepared from the corresponding parent by acylation which is usually carried out using carboxylic acid anhydride or carboxylic acid chloride as the acylation agents. Such acyl groups are lower alkanoyl, benzoyl and substituted benzoyl wherein said substituent is halo, trifluoromethyl, lower alkoxy or phenyl or formyl. Such esters possess the activity of the prostaglandin analog from which they are derived.

The magnesium salts of prostaglandin analogs of the present invention which have a beta hydroxyl at $C_{15}$ and possess a $C_{15}$ lower alkyl group have action which is similar to their epimers. In some cases, however, the selectivity that these compounds display, such as the antiulcer activity of the magnesium salt of 15-epi-16-m-tolyl $PGE_2$ analog, exceeds that of the epimeric compounds.

The new compounds of this invention can be used in a variety of pharmaceutical preparations which contain the compound, and they may be administered in the same manner as natural prostaglandins by a variety of routes, such as intravenous, oral and topical, including aerosol, intravaginal, and intranasal, among others.

To produce bronchodilation or to increase nasal potency, an appropriate dosage form would be an aqueous ethanolic solution of the magnesnium salt of 2-descarboxy-2-(tetrazol-5-yl)-11-desoxy-16-Ar-substituted -ω-tetranor $PGE_1$ or $PGE_2$ employed as an aerosol using fluorinated hydrocarbons as propellant in the amount of from about 3–500 µg/dose.

The magnesium salt of 16-Ar substituted-ω-tetranor-prostaglandin analogs of the $E_0$ and 13,14-dihydro $E_2$ or F series of the present invention are useful hypotensive agents. For treatment of hypertension these drugs could appropriately be administered as an intravenous injection at doses of about 0.5–10 µg/kg or preferably in the form of capsules or tablets at doses of 0.005 to 0.5 mg/kg/day.

The magnesium salts of 15-keto-16-Ar substituted -ω-tetranorprostaglandin analogs or 15-epi-16-ar substituted -ω-tetranorprostaglandin E analogs of the present invention are useful antiulcer agents. For treatment of petic ulcers these drugs may be administered in the form of capsules or tablets at doses of 0.005 to 0.5 mg/kg/day.

To prepare any of the above dosage forms or any of the numerous other forms possible, various reaction-inert diluents, excipients or carriers may be employed. Such substances include, for example, water, ethanol, gelatins, lactose, starches, magnesium stearate, talc, vegetable oils, benzyl alcohols, gums, polyalkylene glycols, petroleum jelly, cholesterol and other known carriers for medicaments. If desired, these pharmaceutical compositions may contain auxiliary substances such as preserving agents, wetting agents, stabilizing agents, or other therapeutic agents such as antibiotics.

The following examples are merely illustrative, and in no way limit the scope of the appended claims. In these examples it will be appreciated that all temperatures are expressed in Centigrade, all melting and boiling points are uncorrected.

EXAMPLE I

Dimethyl 2-Oxo-3-phenylpropylphosphonate

A solution of 6.2 g (50 mmoles) dimethyl methylphosphonate (Aldrich) in 125 ml dry tetrahydrofuran was cooled to −78° in a dry nitrogen atmosphere. To the stirred phosphonate solution was added 21 ml of 2.37 M n-butyllithium in hexane solution (Alfa Inorganics, Inc.) dropwise over a period of 18 minutes at such a rate that the reaction temperature never rose above −65°. After an additional 5 minutes stirring at −78°, 7.5 g (50.0 mmole) methyl was added dropwise at a rate that kept the reaction temperature less than −70° (20 minutes). After 3.5 hours at −78° the reaction mixture was allowed to warm to ambient temperature, neutralized with 6 ml acetic acid and rotary evaporated to a white gel. The gelatonous material was taken up in 75 ml water, the aqueous phase extracted with 100 ml portions of chloroform (3x), the combined organic extracts were backwashed (50 cc $H_2O$), dried ($MgSO_4$), and concentrated (water aspirator) to a crude residue and distilled, b.p. 134°–5° (<0.1 mm) to give 3.5 g (29%) dimethyl 2-oxo-3-phenylpropylphosphonate.

The nmr spectrum ($CDCl_3$) showed a doublet centered at 3.7 δ (J=11.5 cps, 6H) for

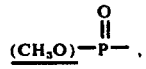

a triplet centered at 3.37 δ (2H) for $CH_3$—O—$CH_2$—$CH_2$—, a singlet at 3.28 δ (3H) for $CH_3$—O—$CH_2$—, a doublet centered at 3.14 δ (J=23 cps, 2H)

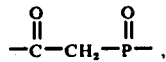

a singlet at 3.9 δ (2H) for

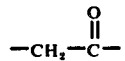

and a broad singlet at 7.2 δ (6H) for $C_6H_5$—.

EXAMPLE II

2-[5α-Hydroxy-2β-(3-oxo-4-phenyl-trans-1-buten-1-yl)-cyclopent-1α-yl]acetic acid, γ-lactone (2a):

Method A:

Dimethyl 2-oxo-3-phenylpropylphosphonate (6.93 g, 28.6 mmole) in 420 ml anhydrous THF was treated with 1.21 g (28.6 mmole) 57% sodium hydride in a dry nitrogen atmosphere at room temperature. After 60 min. of stirring the known 2-[5α-hydroxy-2β-formylcyclopent-1α-yl]acetic acid, γ-lactone (1) in 50 ml anhydrous THF was added. After 95 minutes the reaction mixture was quenched with 4.2 ml glacial acetic acid, filtered, evaporated and combined with 250 ml ethyl acetate which was washed successively with 100 ml saturated sodium bicarbonate solution (2x), 150 ml water (1x), 150 ml satuated brine (1x), dried ($Na_2SO_4$) and evaporated to yield 2.51 g 2-[5α-hydroxy-2β-(3-oxo-4-phenyl-trans-1-buten-1-yl)-cyclopent-1α-yl]acetic acid, γ-lactone (2a) as a solid after column chromatography (Silica gel, Baker, 60–200 mesh), m.p. 52°–56°, $[\alpha]_D^{25}$ =+35.0° (C=0.8, $CHCl_3$).

The nmr spectrum ($CDCl_3$) exhibited a doublet of doublets centered at 6.80 δ (1H, J=7, 16 cps) and a doublet centered at 6.27 δ (1H, J=16 cps) for the olefinic protons, a broad singlet at 7.26 δ (5H) for $C_6H_5$

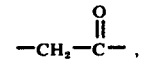

a singlet at 3.82 δ (2H) for $C_6H_5$

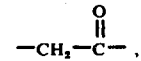

and multiplets at 4.78–5.18 δ (1H) and 1.2–2.8 δ (8H) for the remainder of the protons.

Method B:

To a solution of 6.93 g (28.6 mmoles) of dimethyl 2-oxo-3-phenylpropylphosphonate in 200 ml of 1,2-dimethoxyethane, cooled to 0°, is added 28 ml of a 1.0M solution of n-butyllithium in hexane. The solution is let stir for 5 minutes then 3.85 g (25 mmoles) of the aldehyde 1 is added. The mixture is warmed to room temperature and is stirred for 2 hours, then is quenched by the addition of glacial acetic acid. The quenched reaction is concentrated, then diluted with methylene chloride. The organic layer is washed with saturated $NaHCO_3$, water, and saturated brine, is dried (anhydrous $MgSO_4$), and is concentrated. Purification of the crude product by column chromatography affords the desired 2-[5α-hydroxy-2β-(3-oxo-4-phenyl-trans-1-buten-1-yl)cyclopent-1α-yl]acetic acid, γ-lactone (2a).

EXAMPLE III

2-[5α-hydroxy-2β-(3α-hydroxy-4-phenyl-trans-1-buten-1-yl)-cyclopent 1α-yl]acetic acid, γ-lactone (3a) and

2-[5α-hydroxy-2β-(3β-hydroxy4-phenyl-trans-1-buten-1-yl)-cyclopent-1α-yl]acetic acid, γ-lactone (epi 3a):

To a solution of 2.5 g (9.25 mmole) 2-[5α-hydroxy-2β-(3-oxo-4-phenyl-trans-1-buten-1-yl)cyclopent-1α-yl]acetic acid, γ-lactone (2) in 30 ml dry THF in a dry nitrogen atmosphere at −78° was added dropwise 9.25 ml of a 1.0M lithium triethylborohydride solution. After stirring at −78° for 30 min., 20 ml of acetic acid/water (40:60) was added. After the reaction came to room temperature, 40 ml of water was added and the reaction was extracted with methylene chloride (3×50 ml), washed with brine (2×5 ml), dried ($Na_2SO_4$) and concentrated (water aspirator). The resulant oil was purified by column chromatography on silica gel (Baker "Analyzed" Reagent 60–200 mesh) using cyclohexane and ether as eluents. After elution of less polar impurities a fraction containing 365 mg 2-[5α-hydroxy-2β-(3α-hydroxy-4-phenyl trans-1-buten-1- yl)cyclopent-1α-yl]acetic acid, γ-lactone (3a), a 578 mg fraction of mixed 3a and epi 3a and finally a fraction (489 mg) of 2-[5α-hydroxy-2β-(3β-hydroxy-4-phenyl-trans-1-buten-yl)cyclopent-1α-yl]acid, γ-lactone epi 3a were obtained. The 3a had $[\alpha]_D^{25} = +6.623°$ (C=1.0, CHCl$_3$) and epi 3 had $[\alpha]_D^{25} + 24.305°$ (C=1.69, CHCl$_3$).

The product of this Example (epi 3a) may also be converted to 15-epi or 15-keto-2-descarboxy-2-(tetrazol-5-yl)-16-phenyl 11-desoxy-ω-tetranorprostaglandin E, F$_\alpha$ and F$_\beta$ of the two-, one-, zero- and 13,14-dihydro two- series by the procedures of Examples IV-XII, XXVI, XXIX-XXXII, and XXXVIII.

The products of this Example (3a and epi 3a) may be converted by the procedure of Example XXVI to 7a and epi 7a, intermediates suitable for the preparation of the 2-descarboxy-2-(tetrazol-5-yl)-13,14-dihydro-16-phenyl-11-desoxy-ω-tetranorprostaglandins E$_2$, F$_{2\alpha}$ and F$_{2\beta}$ of this invention.

EXAMPLE IV

2-[5α-Hydroxy-2β-(3α-tetrahydropyran-2-yloxy)-4-phenyl-trans-1-buten-1-yl)cyclopent-1α-yl]acetic acid, γ-lactone (4a)

To a solution of 805 mg (2.96 mmole) 2-[5α-hydroxy-2β-(3α-hydroxy-4-phenyl-trans-1-buten-1-yl]cyclopent-1α-yl]acetic acid, γ-lactone (3a) in 20 ml anhydrous methylene chloride and 0.735 ml of 2,3dihydropyran at 0° in a dry nitrogen atmosphere was added 35.3 mg p-toluenesulfonic acid, monohydrate. After stirring for 35 minutes, the reaction mixture was combined with 150 ml ether, the ether solution washed with saturated sodium bicarbonate (2×100ml) then saturated brine (1×100 ml), dried (Na$_2$SO$_4$) and concentrated to yield 1.2 g (>100%) crude 2-[5α-hydroxy-2β-(3α-(tetrahydropyran2-yloxy)-4-phenyl-trans-1-buten-1yl)cyclopent-1α-yl]acetic acid, γ-lactone (4a).

The ir (CHCl$_3$) spectrum had a medium adsorbition at 975 cm$^{-1}$ for the trans-double bond and a strong adsorbtion at 1770 cm$^{116\ 1}$ of the lactone carbonyl.

EXAMPLE V

2-[5α-Hydroxy-2β-(3α-dimethyl-tert-butylsilyloxy-4-phenyl-trans-1-buten-1-yl)cyclopent-1α-yl]acetic acid, γ-lactone (4a)

A solution of 548 mg (2.0 mmole) of 2-[5α-hydroxy-2β-(3α-hydroxy-4-phenyl-trans-1-buten-1-yl)cyclopent-1α-yl]acetic acid, γ-lactone (3a), 375 mg (2.5 mmole) of dimethyl-tert-butylsilyl chloride, and 340 mg (5.0 mmole) of imidazole in 1.0 ml of dimethylformamide is heated at 35° for 18 hours. The reaction mixture is then diluted with water and the aqueous layer extracted with methylene chloride. The organic extracts are dried (anhydrous MgSO$_4$) and concentrated to provide the desired 2-[5α-hydroxy-2β-(3α-dimethyl-tert-butylsilyloxy-4-phenyl-trans-1-buten-1-yl)cyclopent-1α-yl]acetic acid, γ-lactone (4a).

The product of this Example (4a) may be converted by the procedures of Example XXVI to 7a, an intermediate suitable for the preparation of the 2-descarboxy-2-(tetrazol-5-yl)-13,14-dihydro-16-phenyl-11-desoxy-ω-tetranorprostaglandins E$_2$, F$_{2\alpha}$ and F$_{2\beta}$ of this invention.

EXAMPLE VI

2-[5α-Hydroxy-2β-(3α-(tetrahydropyran-2-yloxy)-4-phenyl-trans-1-buten-1-yl)cyclopent-1α-yl]acetaldehyde, γ-hemiacetal (5a)

A solution of 1.1 g (2.96 mmole) 2-[5α-hydroxy-2β-[3α-(tetrahydropyran-2-yloxy)-4-phenyl-trans-1-buten-1-yl)cyclopent-1α-yl]acetic acid, γ-lactone (4a) in 15 ml dry toluene was cooled to −78° in a dry nitrogen atmosphere. To this cooled solution was added 4.05 ml of 20% diisobutylaluminum hydride in n-hexane (Alfa Inorganics) dropwise at such a rate so that the internal temperature never rose above −65° (15 minutes). After an additional 30 minutes of stirring at −78°, anhydrous methanol was added until gas evolution ceased and the reaction mixture was allowed to warm to room temperature. The reaction mixture was combined with 150 ml ether, washed with 50% sodium potassium tartrate solution (2×50 ml), brine (1×75 ml), dried (Na$_2$SO$_4$) and concentrated to yield 883 mg 2-[5α-hydroxy-2β-(3α-(tetrahydropyran-2-yloxy)-4-phenyl-trans-1-buten-1-yl)cyclopent-1-yl]acetaldehyde, γ-hemiacetal (5a) after column chromatography.

The product of this Example (5a) may be converted by the procedure of Example XXVI to 9a, an intermediate suitable for the preparation of the 2-descarboxy-2-(tetrazol-5-yl)-13,14-dihydro-16-phenyl-11-desoxy-ω-tetranorprostaglandins E$_2$, F$_{2\alpha}$ and F$_{2\beta}$ of this invention.

EXAMPLE VII

5α-hydroxy-2β-[3α-(tetrahydropyran-2-yloxy)-4-phenyl-trans-1-buten-1-yl]-1α-[6-(tetrazol-5-yl)-cis-2-hexen-1-yl]cyclopentane (10a)

To a solution of 4.6 g (9.8 mmole) [4-(tetrazol-5-yl)-n-butyl [triphenylphosphonium bromide in a dry nitrogen atmosphere in 20 ml dry dimethyl sulfoxide was added 9.8 ml (19.6 mmole) of a 2M solution of sodium methylsulfinylmethide in dimethyl sulfoxide. To this red ylide solution was added dropwise a solution of 883 mg (2.46 mmole) 2-[5α-hydroxy-2β-(3α-(tetrahydropyran-2-yloxy)-4-phenyl-trans-1-buten-1-yl)cyclopent-1α-yl]acetaldehyde, γ-hemiacetal (5a) in 10 ml dry dimethyl sulfoxide over a period of 20 minutes. After an additional 1 hour stirring at room temperature the reaction mixture was poured onto ice water, ethyl acetate (150 ml) and 20 ml 1.0N HCl. The acidic solution was further extracted with ethyl acetate (2×75 ml) and the combined organic extracts washed twice with water (100 ml), brine (1×100 ml), dried (MgSO$_4$) and evaporated to a solid residue. The residue was purified by column chromatography on silica gel (Baker Analyzed Reagent 60–200 mesh) using chloroform and ethyl acetate as eluents. After removal of high R$_f$ impurities, 576 mg of 5α-hydroxy-2β-[3α-(tetrahydropyran-2-yloxy)-4-phenyl-trans-1-buten-1-yl]-1α-[6-(tetrazol-5-yl)-cis-2-hexen-1-yl]cyclopentane (10a) was collected.

The product of this Example (10a) may be hydrolyzed as described in Example IX to provide the 2-descarboxy-2-(tetrazol-5-yl)-11-desoxy-16-phenyl-ω-tetranor PGF$_{2\alpha}$ (11a).

This product (11a) may be hydrogenated as described in Examples XI and XII to afford the corresponding PGF$_{1\alpha}$ and PGF$_{0\alpha}$ analogs.

EXAMPLE VIII

2α-[6-(tetrazol-5-yl)-cis-2-hexen-1-yl]-3β-[3α-(tetrahydropyran-2-yloxy)-4-phenyl-trans-1-buten-1-yl]cyclopentanone (12a)

To a solution cooled to −10° under nitrogen of 576 mg (1.24 mmole) (10a) in 20 ml reagent grade acetone was added dropwise to 0.56 ml (1.48 mmole) of Jones' reagent. After 15 minutes at −10°, 0.4 ml 2-propanol was added and the reaction mixture was allowed to stir an additional 5 minutes at which time it was combined with 150 ml ethyl acetate, washed with water (2×50 ml), dried (MgSO$_4$) and concentrated to give 566 mg of the desired 2α-[6-(tetrazol-5-yl)-cis-2-hexen-1-yl]-3β-[3α-(tetrahydropyran-2-yloxy)-4-phenyl-trans-1-buten-1-yl]cyclopentanone (12a) which was used without purification.

Reduction of the product of this Example (12a) by the procedure of Example X followed by hydrolysis as described in Example IX provides the 2-descarboxy-2-(tetrazol-5-yl)-11-desoxy-16-phenyl-ω-tetranor PGF$_{2\alpha}$ and PGF$_{2\beta}$.

EXAMPLE IX

2α-[6-(tetrazol-5-yl)-cis-2-hexen-1-yl]-3β-(3α-hydroxy-4-phenyl-trans-1-buten-1-yl)cyclopentanone (13a)

A solution of 566 mg (12a) in 5.6 ml of a 65:35 mixture of glacial acetic acid:water was stirred under nitrogen at 25° for 18 hours then was concentrated by rotary evaporation. The resultant crude oil was purified by column chromatography on silica gel (Baker 60–200 mish) using chloroform and ethyl acetate as eluents. After elution of less polar impurities the oily 13a weighing 89 mg was collected. The ir (CHCl$_3$) exhibited a strong adsorbtion at 1730 cm$^{-1}$ for the cyclopentanone carbonyl and a medium adsorbtion at 973 cm$^{-1}$ for the trans double bond. The specific rotation (C 0.89, CHCl$_3$) was recorded at three wavelengths: $[\alpha]_D^{25} = -20.8°$; $[\alpha]_{436}^{25} = -73.5°$; $[\alpha]_{365}^{25} = -239.9°$.

EXAMPLE X

5α-hydroxy-2β-[3α-hydroxy-4-phenylbut-1-yl]-1α-[6-(tetrazol-5-yl)hex-1-yl]cyclopentane and
5β-hydroxy-2β-[3α-hydroxy-4-phenylbut-1-yl]-1α-[6-(tetrazol-5-yl)hex-1-yl]cyclopentane To a solution, cooled to 0°, of 100 mg of the 2α-[6-(tetrazol-5-yl)hex-1-yl]-3β-[3α-hydroxy-4-phenylbut-1-yl]cyclopentanone in 10 ml of methanol is added a cooled solution of 300 mg of sodium borohydride in 35 ml of methanol. The mixture is stirred at 0°–5° for 30 minutes then 2 ml of water is added. After removal of the methanol by rotary evaporation, the aqueous layer is overlaid with ethyl acetate and is acidified to pH 3 with 10% HCl. The aqueous layer is extracted with ethyl acetate and the combined organic extracts are washed with water and saturated brine, are dried (anhydrous MgSO$_4$), and are concentrated. Purification of the crude product by column chromatography affords the desired 5α-hydroxy-2β-[3α-hydroxy-4-phenylbut-1-yl]-1α-[6-(tetrazol-5-yl)hex-1-yl]-cyclopentane and 5β-hydroxy-2β-[3α-hydroxy-4-phenylbut-1-yl]-1α-[6-(tetrazol-5-yl)hex-1-yl]cyclopentane.

EXAMPLE XI

2α-[6-(tetrazol-5-yl)hex-1-yl]-3β-[3α-hydroxy-4-phenylbut-1-yl]-cyclopentanone

A mixture of 500 mg of 2α-[6-(tetrazol-5-yl)-cis-2-hexen-1-yl]-3β-[3α-hydroxy-4-phenyl-trans-1-buten-1-yl]cyclopentanone and 50 mg of 10% palladium on carbon in 50 ml of ethyl acetate is stirred under 1 atmosphere of hydrogen for 3 hours. The mixture is filtered and the filtrate concentrated to provide, after purification by column chromatography, the 2α-[6-(tetrazol-5-yl)-hex-1-yl]-3β-[3α-hydroxy-4-phenylbut-1-yl]-cyclopentanone.

EXAMPLE XII

2α-[6-(tetrazol-5-yl)hex-1-yl]-3β-[3α-hydroxy-4-phenyl-trans-1-buten-1-yl]cyclopentanone A solution of 46 mg 2α-[6-(tetrazol-5-yl)-cis-2-hexen-1-yl]-3β-[3α-hydroxy-4-phenyl-trans-1-buten-1-yl]cyclopentanone in 5 ml of dry ether is treated with 448 mg (3.6 mmole) dimethyl isopropyl chlorosilane and 360 mg (3.6 mmole) triethylamine at 25° for 48 hours. The reaction mixture is cooled to 0°, methanol is added and the resulting solution is washed with water (3 × 2 ml), dried (MgSO$_4$) and evaporated to a residue (67 mg). The crude residue is then taken up in 6 ml methanol and 30 mg of 5% Pd/C and the resultant slurry is hydrogenated for 4 hours at −22° (CCl$_4$/Dry Ice). After filtration through super cell and evaporation, the hydrogenated product is hydrolyzed in 2 ml of acetic cid-water (3:1) for 10 minutes, diluted with water (20 ml) and extracted with ethyl acetate (4 × 15 ml). The combined organic extracts are washed with water (2 × 10 ml), dried (MgSO$_4$) and evaporated to yield 2α-[6-(tetrazol-5-yl)hex-1-yl]-3β-[3α-hydroxy-4-phenyl-trans-1-buten-1-yl]cyclopentanone after column chromatography.

EXAMPLE XIII

2-[2β-benzyloxymethyl-5α-hydroxycyclopent-1α-yl]acetaldehyde, γ-hemiacetal (21)

To a solution, cooled to −78° under nitrogen, of 10.0 g (40.5 mmoles) of the known 2-[2β-benzyloxymethyl-5α-hydroxycyclopent-1α-yl]acetic acid, γ-lactone in 100 ml of toluene was added 55.5 ml of a 20% solution of diisobutylaluminum hydride in hexane (Alfa). The solution was stirred for 40 minutes then was quenched in the cold by the dropwise addition of methanol until gas evolution ceased. The quenched reaction mixture was let warm to room temperature, then was concentrated. The resultant oil was slurried in hot methanol, filtered, and the filtrate was concentrated. Purification of the crude product by silica gel chromatography using mixtures of benzene: ethylacetate as eluents afforded the desired 2-[2β-benzyloxymethyl-5α-hydroxycyclopent-1α-yl]acetaldehyde, γ-hemiacetal (21a) as a viscous oil weighing 8.91 g (86% yield).

EXAMPLE XIV

5α-hydroxy-2β-benzyloxymethyl-1α-[6-(tetrazol-5-yl)-cis-2-hexen-1-yl]cyclopentene (23a)

To a solution of 11.7 g (25.0 mmoles) of [4-(tetrazol-5-yl)-butyl]triphenylphosphonium bromide in 25 ml of dimethyl sulfoxide was added dropwise 27 ml of a 1.81 M solution of sodium methylsulfinylmethide in dimethyl sulfoxide. To the resultant red ylide solution was added a solution of 2.48 g (10.0 mmoles) of the 2-[2β-benzyloxymethyl-5α-hydroxycyclopent-1α-yl]acetaldehyde, γ-hemiacetal (21a) in 20 ml of dimethyl sulfoxide. After being stirred for 1.5 hours under nitrogen at room temperature the reaction was poured onto ice-water. The basic aqueous solution was extracted with a 2:1 mixture of ethyl acetate: ether was then laid with ethyl acetate, was acidified to pH 3 with 10% aqueous hydrochloric acid, and was extracted with ethyl acetate. The combined ethyl acetate extracts were washed with water, dried (anhydrous magnesium sulfate), and concentrated. The crude product was dissolved in ethyl acetate and was let crystallize. Concentration of the filtrate provided the desired 5α-hydroxy-2β-benzyloxymethyl-1α-[6-(tetrazol-5-yl)-cis-2-hexen-1-yl]cyclopentane (23a) weighing 5.32 g which was used without purification.

EXAMPLE XV

5α-acetoxy-2β-benzyloxymethyl-1α-[6-(tetrazol-5-yl)-cis-2-hexen-1-yl]cyclopentane A mixture of 5.32 g (10.0 mmoles) of the crude alcohol of Example XIV, 30.0 ml of pyridine and 4.43 ml (46.8 mmoles) of acetic anhydride was stirred under nitrogen at 50° for 5.5 hours. The mixture was poured onto 200 ml of cold 6N hydrochloric acid. The aqueous layer was extracted with ethyl acetate. The organic extracts were washed with water and saturated brine, were dried (anhydrous magnesium sulfate), and were concentrated. Purification of the crude product by silica gel chromatography using mixtures of benzene: ethyl acetate as eluents provided the desired 5α-acetoxy-2β-benzyloxymethyl-1α-[6-(tetrazol-5-yl)-cis-2-hexen-1-yl]cyclopentane weighing 2.78 g (70% yield).

EXAMPLE XVI

5α-acetoxy-2β-hydroxymethyl-1α-[6-(tetrazol-5-yl)-hex-1-yl]-cyclopentane

A heterogeneous mixture of 2.38 g (5.97 mmoles) of the chromatographed benzyl ether of Example XV, 500 mg of 10% palladium on carbon, and 24 ml of a 20:1 mixture of absolute ethanol:glacial acetic acid was stirred at room temperature under one atmosphere of hydrogen for 19 hours. The mixture was then filtered through Celite 545 and the filtrate was concentrated and was azetroped under reduced pressure with toluene to provide the desired 5α-acetoxy-2β-hydroxymethyl-1α-[6-(tetrazol-5-yl)-hex-1-yl]cyclopentane weighing 1.74 g (94% yield), which was recrystallized from ethyl acetate: hexane (m.p. 65.5°–66°).

EXAMPLE XVII

5α-acetoxy-2β-formyl-1α-[6-(tetrazol-5-yl)-hex-1-yl]cyclopentane (24a)

To a stirred solution of 3.88 ml (48.0 mmoles) of pyridine in 58 ml of methylene chloride, cooled to 10° to 15° under nitrogen, was added portionwise over a period of 30 minutes 2.40 g (24.0 mmoles) of chromium trioxide. The dark burgundy solution was let warm to room temperature then was cooled to 0°. To the cold solution was added a solution of 930 mg (3.0 mmoles) of the alcohol of Example XVI in 9.0 ml of methylene chloride with the concomitant formation of a dense black precipitate. The suspension was stirred in the cold for 45 minutes then 8.30 g (60.0 mmoles) of finely ground sodium bisulfite monohydrate was added. After being stirred for 10 minutes 7.22 g (60.0 mmoles) of anhydrous magnesium sulfate was added. After being stirred for 5 minutes the dark suspension was filtered through a pad of Celite, was washed with methylene chloride, then was concentrated. Purification of the crude product by silica gel chromatography using a 1:1 mixture of methylene chloride: ethyl acetate as eluent afforded the desired 5α-acetoxy-2β-formyl-1α-[6-(tetrazol-5-yl)-hex-1-yl] cyclopentane (24a) as a colorless oil weighing 633 mg (69.0% yield).

EXAMPLE XVIII

5α-acetoxy-2β-(3-oxo-4-phenyl-trans-1-buten-1-yl)-1α-[6-(tetrazol-5-yl)-hex-1-yl]cyclopentane To a suspension of 260 mg (6.18 mmoles) of a 57.0% dispersion of sodium hydride in mineral oil in 30 ml of tetrahydrofuran was added 1.58 g (6.18 mmoles) of the known dimethyl-2-oxo-3-phenylpropylphosphonate. The mixture was stirred at room temperature for 20 minutes under nitrogen with the concomitant formation of a yellow precipitate. To this suspension was added a solution of 6.33 mg (2.06 mmoles) of the aldehyde of Example XVII in 5 ml of tetrahydrofuran. The solution was stirred at room temperature for 50 minutes under nitrogen then was quenched by the addition of glacial acetic acid to pH 5 and was concentrated. The resultant mixture was dissolved in ethyl acetate; the organic layer was washed with water and saturated brine, was dried (anhydrous magnesium sulfate), and was concentrated. Purification of the crude product by dry column chromatography (silica gel) afforded the desired 5α-acetoxy-2β-(3-oxo-4-phenyl-trans-1-buten-1-yl)-1α-[6-(tetrazol-5-yl)-hex-1-yl]cyclopentane as a colorless oil weighing 533 mg (61% yield).

EXAMPLE XIX

5α-acetoxy-2β-(3α-hydroxy-4-phenyl-trans-1-buten-1-yl)-1α-[6-(tetrazol-5-yl)hex-1-yl]cyclopentane To a solution, cooled to −78°, of 849 mg (2.0 mmoles) of the enone of Example XVIII in 20 ml of tetrahydrofuran is added 4.0 ml (4.0 mmoles) of a 1.0 M solution of lithium tri-ethylborohydride in tetrahydrofuran. The solution is stirred at −78° under nitrogen for 0.5 hour then is quenched by the addition of 10 ml of 40% aqueous acetic acid. The quenched reaction mixture is let warm to room temperature and is extracted with ethyl acetate; the combined organic extracts are washed with water and saturated brine, and dried (anhydrous magnesium sulfate), are concentrated, and azeotroped with toluene. Purification of the crude product by silica gel chromatography provides the 5α-acetoxy-2β-(3α-hydroxy-4-phenyl-trans-1-buten-1-yl)-1α-[6-(tetrazol-5-yl)-hex-1-yl]cyclopentane and the 5α-acetoxy-2β-(3β-hydroxy-4-phenyl-trans-1-buten-1-yl)-1α-[6-(tetrazol-5-yl)hex-1-yl]cyclopentane.

The 5α-acetoxy-2β-(3β-hydroxy-4-phenyl-trans-1-buten-1-yl)-1α-[6-(tetrazol-5-yl)hex-1-yl]cyclopentane may be converted by the procedures in Example XX-XXIII to 11-deshydroxy-15-epi-2-descarboxy-2-(tetrazol-5-yl)PGE$_1$ and PGF$_{1\alpha}$.

EXAMPLE XX

5α-hydroxy-2β-(3α-hydroxy-4-phenyl-trans-1-buten-1-yl)-1α-[6-(tetrazol-5-yl)-hex-1-yl]cyclopentane (17a)

A solution of 424 mg (1.00 mmole) of the alcohol of Example XIX, 3.0 ml (3.0 mmoles) of 1.0 N aqueous sodium hydroxide, 3.0 ml of tetrahydrofuran, and 3.0 ml of absolute methanol is stirred under nitrogen at room temperature for 2.5 hours. The solution is then acidified by the addition of 3.0 ml of 1.0N hydrochloric acid and is extracted with ethyl acetate. The combined organic extracts are dried (anhydrous magnesium sulfate and concentrated. Purification of the crude product by silica gel chromatography provides the desired 5α-hydroxy-2β-(3α-hydroxy-4-phenyl-trans-1-buten-1-yl)-1α-[6-(tetrazol-5-yl)-hex-1-yl]cyclopentane.

EXAMPLE XXI

5α-acetoxy-2β-(3α-(tetrahydropyran-2-yloxy)-4-phenyl-trans-1-buten-1-yl)-1α-[6-(tetrazol-5-yl)-hex-1-yl]cyclopentane A solution of 250 mg of the alcohol of Example XIX, 0.250 ml of dihydropyran, 2.5 ml of methylene chloride, and 2.5 mg of p-toluenesulfonic acid monohydrate is stirred at room temperature under nitrogen for 15 minutes. The reaction mixture is then diluted with ether, washed with water, is dried (anhydrous magnesium sulfate), and is concentrated to provide the desired 5α-acetoxy-2β-(3α-(tetrahydropyran-2-yloxy)-4-phenyl-trans-1-buten-1-yl)-1α-[6-(tetrazol-5-yl)-hex-1-yl]cyclopentane.

EXAMPLE XXII

5α-hydroxy-2β-(3α-(tetrahydropyran-2-yloxy)-4-phenyl-trans-1-buten-1-yl)-1α-[6-(tetrazol-5-yl)-hex-1-yl]cyclopentane A homogeneous solution of 221 mg (0.436 mmole) of the crude THP ether of Example XXI, 1.30 ml (1.30 mmoles) of a 1.0N aqueous sodium hydroxide solution, 1.3 ml of methanol, and 1.3 ml of tetrahydrofuran is stirred at room temperature overnight. The reaction mixture is then quenched by the addition of 1.30 ml (1.30 mmoles) of a 1.0 N aqueous hydrochloric acid solution and is diluted with ethyl acetate. The organic layer is dried (anhydrous magnesium sulfate) and concentrated. Purification of the crude product by silica gel chromatography affords the desired 5α-hydroxy-2β-(3α-(tetrahydropyran-2-yloxy)-4-phenyl-trans-1-buten-1-yl)-1α-[6-(tetrazol-5-yl)hex-1-yl]cyclopentane.

EXAMPLE XXIII

1α-[6-(tetrazol-5-yl)-hex-1-yl]-2β-(3α-(tetrahydropyran-2-yloxy)-4-phenyl-1-buten-1-yl)cyclopentanone To a solution, cooled to 23° under nitrogen, of 178 mg (0.371 mmole) of the alcohol of Example XXII in 4.0 ml of acetone is added dropwise 0.163 ml (0.408 mmole) of Jones' reagent. The reaction is stirred in the cold for 15 minutes then is quenched by the addition of 0.163 ml of isopropyl alcohol. The quenched by the addition of 0.163 ml of isopropyl alcohol. The quenched reaction is stirred in the cold for 5 minutes then is diluted with ethyl acetate. The organic solution is washed with water, is dried (anhydrous magnesium sulfate), and is concentrated to afford the desired 1α-[6-(tetrazol-5-yl)hex-1-yl]-2β-(3α-tetrahydropyran-2-yloxy)-4-phenyl-trans-1-buten-1-yl)cyclopentanone which is used without purification.

EXAMPLE XXIV

1α-[6-tetrazol-5-yl)-hex-1-yl]-2β-(3α-hydroxy-trans-4-phenyl-1-buten-1-yl)cyclopentanone A homogeneous solution of 0.190 g of the crude THP ether of Example XXIII in 2.0 ml of a 65:35 mixture of glacial acetic acid: water is stirred under nitrogen at room temperature for 12 hours, then is concentrated and azeotroped with toluene. Purification of the crude product by silica gel chromatography affords the desired 1α-[6-(tetrazol-5-yl)hex-1-yl]-2β-(3α-hydroxy-4-phenyl-trans-1-buten-1-yl)cyclopentanone.

EXAMPLE XXV

2-[5α-hydroxy-2β-(3-oxo-4-(m-tolyl)but-1-yl)cyclopent-1α-yl]-acetic acid, γ-lactone (6b)

A mixture of 6.8 g (23 mmoles) of 2-[5α-hydroxy-2β-(3-oxo-4-(m-tolyl)-trans-11 -buten-11 -yl)cyclopent-1α-yl]acetic acid, γ-lactone, (2b)50 ml of ethyl acetate, and 670 mg of 10% palladium on carbon was hydrogenated on a Parr shaker. The mixture was filtered and the filtrate concentrated to provide 6.8 g of the desired 2-[5α-hydroxy-2β-(3-oxo-4-(m-tolyl)but-11 -yl)cyclopent-1α-yl]acetic acid, γ-lactone (6b) as an oil which crystallized upon standing (m.p. 60°–62°).

The ir spectrum ($CHCl_3$) of 6b exhibited strong absorptions at 1765 and 1700 $cm^{-1}$.

The product of this Example (6b) may be converted to the 2-descarboxy-2-(tetrazol-5-yl)-11-desoxy-16-(m-tolyl)-13,14-dihydro-ω-tetranor $PGE_2$, $PGF_{2\beta}$, and $PGF_{2\alpha}$ analogs of this invention by the procedures of Examples III-IX, X-XII, XXVIII, XXIX-XXXII, and XXXVIII.

EXAMPLE XXVI

21 -[5α-hydroxy-2β-(3α-(tetrahydropyran-21 -yloxy)-4-(m-tolyl)but-11 -yl)cyclopent-1α-;yl]acetic acid, γ-lactone (8b)

A mixture of 2.4 g (6.1 mmole) of 2 -[5α-hydroxy-2β-(3α-(tetrahydropyran-2-yloxy)-4-(m-tolyl)-trans-1-buten-1-yl)cyclopent-1α-yl]acetic acid, γ-lactone (4b), 50 ml of ethyl acetate, and 250 mg of 10% palladium on carbon was hydrogenated on a Parr shaker. The reaction mixture was then filtered and the filtrate concentrated to provide 2.4 g of the desired 2-[5α-hydroxy-2β-(3α-(tetrahydropyran-2-yloxy)-4-(m-tolyl)but-1-yl)cyclopent-1α-yl]acetic acid, γ-lactone (8b) as a colorless oil which was used without purification.

The ir spectrum ($CHCl_3$) of 8b exhibited a strong absorption at 1770 $cm^{-1}$.

The product of this Example (8b) may be converted by the procedures of Examples VII-X, XXVIII, and XXXIX-XXXII to the 2-descarboxy-2-(tetrazol-5-yl)-11-desoxy-13,14-dihydro-16-(m-tolyl)-ω-tetranor $PGE_2$, $PGF_{2\alpha}$, and $PGF_{2\beta}$ analogs of this invention.

EXAMPLE XXVII

2α-[6-(tetrazol-5-yl)hex-11 -yl]-3β-[3α-tetrahydropyran-2-yloxy)-4-phenylbut-1-yl]cyclopentanone A mixture of 618 mg of the product of Example VIII, 100 ml of methanol, and 135 mg of 10% palladium on carbon was hydrogenated on a Parr shaker for 1.0 hour. The mixture eas then filtered through "Super Cell" and the filtrate was concentrated to provide the desired 2α-[6-(tetrazol-5-yl)hex-1-yl]-3β-[3α-(tetrahydropyran-2-yloxy)-4-phenylbut-1-yl]cyclopentanone which was used without purification.

EXAMPLE XXVIII

2α-[6-(tetrazol-5-yl)-cis-2-hexen-1-yl]-3β-(3-oxo-4-(m-tolyl)-trans-1-buten-1-yl)cyclopentanone To a solution cooled to −10° under nitrogen of 394 mg (1 mmole) 2α-[6-(tetrazol-5-yl)-cis-2-hexen-1-yl]-3β-(3β-hydroxy-4-(m-tolyl)-trans-1-buten-1-yl)cyclopentanone in 20 ml of reagent grade acetone was added dropwise 0.52 ml (1.1 mmole) of Jones' reagent. After 3 minutes at −10°, 0.3 ml of 2-propanol was added and the reaction was combined with 150 ml ethyl acetate, washed with water (2×50 ml), dried (MgSO$_4$) and concentrated to give 400 mg of crude product which was purified by column chromatography to yield 300 mg 2α-[6-(tetrazol-5-yl)-cis-2-hexen-1-yl]-3β-(3-oxo-4-(m-tolyl)-trans-1-buten-1-yl)cyclopentanone.

EXAMPLE XXIX

5α-acetoxy-2β-[3α-(tetrahydropyran-2-yloxy)-4-(m-tolyl)-trans-1-buten-1-yl]-1α-[6-(tetrazol-5-yl)-cis-2-hexen-1-yl]cyclopentanone A solution of 300 mg (.62 mmole) 5α-hydroxy-2β-1-[3α-(tetrahydropyran-2-yloxy)-4-(m-tolyl)-trans-1-buten-1-yl]-1αl-[6-(tetrazol-5-yl)-cis-2-hexen-1-yl]cyclopentane in 1.9 ml pyridine containing 0.28 ml acetic anhydride was stirred at 50° in a dry nitrogen atmosphere for 5 hrs. The reaction was then poured onto 10 ml of ice-cold 6N hydrochloric acid. The aqueous layer was extracted with EtOAc (4 × 10 ml) and the combined extract washed with brine, dried over Na-$_2$SO$_4$ and concentrated to give 306 mg of the desired 5α-l-acetoxy-2β-[3α-(tetrahydropyran-2-yloxy)-4-(m-tolyl)-trans-1-buten-1-yl]-1α-[6-(tetrazol-5-yl)-cis-2-hexen-1-yl]cyclopentane.

EXAMPLE XXX

5α-acetoxy-2β-[3α-hydroxy-4-(m-tolyl)-trans-1-buten-1-yl]-1α-[6-(tetrazol-5-yl)-cis-2-hexen-1yl]cyclopentane A solution of 306 mg 5α-1-acetoxy-2β-[3α-(tetrahydropyran-2-yloxy)-4-(m-tolyl)-trans-1-buten-1-yl]cyclopentane in 5 ml of a 65:35 mixture of glacial acetic acid:water was stirred under nitrogen at 25° for 18 hrs. then was concentreated by rotary evaporation. The resultant crude oil was purified by column chromatography on silica gel (Baker 60–200 mesh) using methylene chloride and ethyl acetate as eluents. After elution of less polar impurities, 85 mg of the desired 5α-acetoxy-2β-[3α-hydroxy-4-(m-tolyl)trans-1-buten-2-l-yl]-1α-[6-(tetrazol-5-yl)-cis-2-hexen-1yl]cyclopentane was collected. The ir (CHCl$_3$) exhibited a strong absorptions at 1720 cm$^{-1}$ for the ester carbonyl and broad absorption at 3550 cm$^{-1}$ for the hydroxyl.

EXAMPLE XXXI

5α-acetoxy-2β-[3-oxo-4-(m-tolyl)-trans-1-buten-1-yl]-1α-6-(tetrazol-5-yl)-cis-2-hexen-1-yl]cyclopentane:

To a solution cooled to −10° under nitrogen of 85 mg (0.2 mmole) 5α--acetoxy-2β-[3α-hydroxy-4-(m-tolyl)-trans-1-buten-1-yl]-1α-[6-(tetrazol-5-yl)-cis-2-hexen-1-yl]cyclopentane in 2.5 ml of reagent grade acetone was added dropwise 73μl of Jones' reagent. After 3 minutes at −10°, 1 drop of 2-propanol was added and the reaction combined with 50 ml ethyl acetate, was washed with water (2 × 25 ml) dried (Na$_2$SO$_4$) and concentrated to give 80 mg of the desired 5α-acetoxy-2β-[3-oxo-4-(m-tolyl)-trans-1-buten-1-yl]-1α-[-6-(tetrazol-5-yl)-cis-2-hexen-1-yl]cyclopentane. The ir (CHCl-hd 3) exhibited a strong absorption at 1710 cm$^{-1}$ for the ester carbonyl and absorption at 1675, 1650 and 1605 for the enone carbonyl.

EXAMPLE XXXII

5α-hydroxy-2β-[3-oxo-4-(m-tolyl)-trans-1buten-1-yl]-1α-(6-(tetrazol-5-yl)-cis-2-hexen-1-yl]cyclopentane A solution of 80 mg (0.18 mmole) 5α-acetoxy-2β-[3-oxo-4-(m-tolyl)-trans-1-buten-1-yl]-1α-[6-(tetrazol-5-yl)-cis-2-hexen-1-yl] cyclopentane in 2 ml of 1.0N aqueous sodium hydroxyl and 1.5 ml of methanol was stirred for 8 hrs. in a dry nitrogen atmosphere. The reaction was concentrated by rotary evaporation and purified by column chromatography on silica gel elutery with methylene and chloride and ethyl acetate. After elution of less polar impurities, 18 mg of 5α-hydroxy-2β-2hexenyl]cyclopentane was collected. The ir(CHCl$_3$) spectrum exhibited strong absorption at 1700 and 1600 cm$^{-1}$ for the enone and broad absorption at 355 cm$^{-1}$ for the hydroxyl.

EXAMPLE XXXIII

2-[5α-hydroxy-2β-(3-(1,4-dioxolane)-4-(m-tolyl)but-1yl)cyclopent-1α-yl]acetic acid, γ-lactone A solution of 2.83 g (9.9 mmole) of 2-[5α-hydroxy-2β-(3-oxo-4-(m-tolyl)but-1-yl)cyclopent-1-α-yl]acetic acid, γ-lactone, 6.2 g (100 mmole) ethylene glycol and 100 mg p-toluenesulfonic acid in 30 ml benzene was heated at reflux with azeotropic removal of water (Dean-Stark trap). The reaction mixture was cooled, washed with saturated sodium bicarbonate, dried over Na$_2$SO$_4$ and evaporated to give 3.2 g of the desired 2-[5α-hydroxy-2β-(3-(1,4-dioxolane)-4-(mtolyl)but-1-yl)cyclopent-1α-yl]acetic acid γ-lactone as an oil.

The ir spectrum (CHCl$_3$) exhibited strong absorption at 1765 cm$^{-1}$.

EXAMPLE XXXIV

2-[5α-hydroxy-2β-(3-(1,4-dioxolane)-4-(m-tolyl)but-1-yl)cyclopent-1α-yl]acetaldehyde, γ-hemiacetal A solution of 3.2 g (9.7 mmole) 2-[5α-hydroxy-2β-(3-(1,4-dioxalane)-4-(m-tolyl)but-1-yl)cyclopent-1α-yl]acetic acid γ-lactone in 150 ml dry toluene was cooled to −78° in a dry nitrogen atmosphere. To this cooled solution was added 13.34 ml of 20% diisobutylaluminum hydride in n-hexane (Alfa Inorganics) dropwise at such a rate so that the internal temperature never rose above −65° (15 min.). After an additional 30 min. at −78°, the reaction was poured onto ether, washed with saturaged sodium, potassium tartrate solvent dried over MgSO$_4$ and evaporated to afford 3.0 g of desired 2-[5α-hydroxy-2β-(3-(1,4-dioxolane)-4-(m-tolyl)but-1-yl)cyclopent-1α-yl] acetaldehyde, γ-hemiacetal after column chromatography.

EXAMPLE XXXV

5α-hydroxy-2β-3-(1,4-dioxolane)-4-(m-tolyl)but-1-yl]-1α-[6-(tetrazol-5-yl)-cis-2-hexen-1-yl]cyclopentane To a solution of 16.81 g (36 mmole) (4-(tetrazol-5-yl)-n-butyl)triphenylphosphonium bromide in a dry nitrogen atmosphere in 100 ml of dry dimethylsulfoxide was added 32.6 ml (68 mmole) of a 2M solution of sodium methylsulfinylmethide in dimethyl sulfoxide. To this red ylide solution was added dropwise a solution of 3.0 g (9 mmole) 2-[5α-hydroxy-2β-(3-(1,4-dioxolane)-4-(m-tolyl)but-1-yl)cyclopent-1α-yl]acetaldehyde, γ-hemiacetal in 10 ml of dry dimethylsulfoxide. After one hr. stirring at room temperature, the reaction mixture was poured onto ice water and ethyl acetate. This mixture was acidified (1N HCl) with vigorous stirring. The acidic solution was further extracted with ethyl acetate and the combined ethyl acetate extracts were evaporated to a solid residue. The residue was purified by column chromatography on silica gel (Baker "Analyzed" Reagent 60-200 mesh) using benzene and ethyl acetate as eluents. After removal of higher $R_f$ impurities, 450 mg of 5α-hydroxy-2β-(3-(1,4-dioxolane)-4-(m-tolyl)-but-1-yl]-1α-[6-(tetrazol-5-yl)-cis-2-hexen-1-yl]cyclopentane was collected.

EXAMPLE XXXVI

2α-[6-(tetrazol-5-yl)-cis-2-hexen-1-yl]-3β-(3-(3-(1,4-dioxolane)-4-(m-tolyl)but-1-yl]cyclopentanone To a solution cooled to −10° under nitrogen of 420 mg (0.95 mmole) 5αhydroxy-2β-(3-(1,4-dioxolane)-4-(m-tolyl)but-1-yl]-1α-[6-(tetrazol-5-yl)-cis-2-hexen-1-yl]cyclopentane was added dropwise 0.4 ml (1.0 mmole) of Jones' reagent. After 15 min. at −10°, 1 washed with water, dried over MgSO₄ and concentrated to give 400 ml of desired product which was used without purification.

EXAMPLE XXXVII

2α-[6-(tetrazol-5-yl)-cis-2-hexen-1-yl]-3β-3-oxo-4-(m-tolyl)but-1-yl]cyclopentanone A solution of 400 mg of 2α-[6-(tetrazol-5-yl)-cis-2-hexane-1-yl]-3β-(3-(1,4-dioxolane)-4-(m-tolyl)but-1-yl]cyclopentanone in 5 ml of a 65:35 mixture of glacial acetic acid:water was stirred under nitrogen at 25° for 18 hrs. then when concentrated by rotary evaporation. The resultant crude oil was purified by column chromatography on silica gel (Mallincrodt CC-7) using methylene chloride and ether as eluents. After elution of less polar impurities, the oily product weighing 100 mg was obtained.

The ir spectrum exhibited a strong absorption at 1730 cm⁻¹ and 1700 cm⁻¹ for the carbonyls.

EXAMPLE XXXVIII

2α-[6-(tetrazol-5-yl)-cis-2-hexen-1-yl]-3β-[3α-hydroxy-4-phenyl-trans-1-buten-1-yl]cyhclopentanone A mixture of 494 mg (1.0 mmole) of 2α-[6-(tetrazol-5-yl)-cis-2-hexen-yl]-3β-[3α-(dimethyl-tert-butyl-silyloxy)-4-phenyl-trans-1-buten-1-yl]cyclopentanone and 522 mg (2.0 mmole) of tetra-n-butylammonium fluoride in 5 ml of tetrahydrofuran is stirred at 0° for 5 minutes then 25° for 30 minutes. The mixture is then diluted with water and extracted with ethyl acetate. The combined organic extracts are washed with saturated brine, dried (anhydrous MgSO₄) and concentrated to provide. after chromatographic purification, 2α-[6-(tetrazol-5-yl)-cis-2-hexen-1-yl]-3β-[3β-hydroxy-4-phenyltrans-1-buten-1-yl]cyclopentanone.

EXAMPLE XXXIX

5α-hydroxy-2β-[3α-(tetrahydropyran-2-yloxy)-4-phenyl-trans-1-buten-1-yl]-1α-[6-(tetrazol-5-yl)hex-1-yl]cyclopentane A solution of the product of Example VII (250 mg) and 25 mg of 5% palladium on carbon in 2.5 ml of methanol, cooled to −20°, is stirred under one atmosphere of hydrogen for 3 hours. The mixture is filtered and the filtrate is concentrated to afford the crude 5α-hydroxy-2β-[3α-(tetrahydropyran-2-yloxy)-4-phenyl-trans-1-buten-1-yl]-1α-[6-(tetrazol-5-yl)hex-1yl]cyclopentane which is used without purification.

The product of this Example may be hydrolyzed as described in Example IX to provide after chromatic purification 2-descarboxy-2-(tetrazol-5-yl)-16-phenyl-11-desoxy-ω-tetranor PGF₁α. The product of this Example may also be converted to 2-descarboxy-2-(tetrazol-5-yl)-16-phenyl-11-desoxy-ω-tetranor PGE₂ by the procedures of Examples VIII-IX.

Additional Compounds

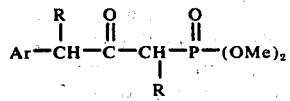

| Ar | R | bp/mp | Rotation | NMR (Jeps) |
|---|---|---|---|---|
| m-methylphenyl | H | 158–162°/0.4mm | | 3.75 (11.5)*, 3.02 (22)** |
| o-biphenyl | H | purified by column chromatography | | 3.74 (11.5)*, 3.05 (22)** |
| 5-phenyl-2-thienyl | H | mp 64–65° | | 3.75 (11.5)*, 3.08 (22)** |
| β-naphthyl | H | mp 45–47° | | 3.73 (11.5)*, 3.10 (22)** |
| p-chlorophenyl | H | purified by column chromatography | | 3.76 (11.5)*, 3.15 (22)** |
| p-t-butylphenyl | H | 180° −/0.2 mm | | 3.74 (11.5)*, 3.11 (22)** |
| phenyl | (+(Me | purified by column chromatography | +205(CHCl₃) | 3.78 (11.5)* 3.26 (22)** / 3.71 (11.5)*, 2.93 (22)** |
| phenyl | (−)Me | purified by column chromatography | −233(CHCl₃) | 3.78 (11.5)* 3.26 (22)** / 3.71 (11.5)*, 2.93 (22)** |

*methoxy protons

-continued

Additional Compounds

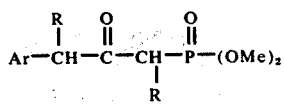

| Ar | R | bp/mp | Rotation | NMR (Jeps) |
|---|---|---|---|---|
| **CCH$_2$—P(O)(O) | | | | |

Additional Compounds of the Structure

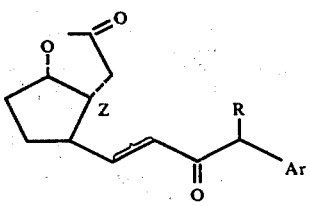

| Ar | Z* | R | mp | IR data cm$^{-1}$ | Rotation |
|---|---|---|---|---|---|
| m-methylphenyl | D | H | 80.5–82.5 | 1770, 1680, 1620, 980 | |
| o-biphenyl | D | H | 51–52° | 1770, 1675, 1620, 980 | |
| 5-phenyl-2-thienyl | D | H | oil | 1775, 1700, 1680, 1640, 980 | |
| β-naphthyl (rac.) | D | H | oil | 1770, 1700, 1680, 1620, 970 | |
| p-chlorophenyl | D | H | oil | 1779, 1709, 1672, 1639, 980 | |
| p-t-butylphenyl | D | H | oil | 1770, 1695, 1675, 1635, 975 | |
| phenyl | D | (+)Me | oil | 1770, 1710, 1620, 975 | +112.1 (CHCl$_3$) |
| phenyl | D | (−)Me | 55–58° | 1770, 1710, 1620, 975 | −32.79 (CHCl$_3$) |

*D=trans double bond; S=single bond

Additional Compounds

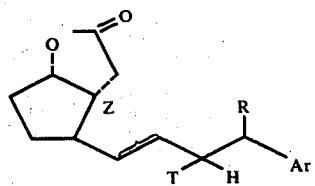

| Ar | R | T | Z$^{(a)}$ | Polarity$^{(b)}$ | SS$^{(c)}$ | IR data cm$^{-1}$ |
|---|---|---|---|---|---|---|
| m-methylphenyl | H | α-OH | D | LP | H0/Et$_2$O | 1770, 970, 3600 |
| m-methylphenyl | H | β-OH | D | MP | | 1770, 970, 3600 |
| o-biphenyl | H | α-OH | D | LB | H0/Et$_2$O | 1770, 975, 3600 |
| o-biphenyl | H | β-OH | D | MP | | 1770, 975, 3600 |
| 5-phenyl-2-thienyl | H | α-OH | D | LP | H0/Et$_2$O | 1770, 975, 3600 |
| 5-phenyl-2-thienyl | H | β-OH | D | MP | | 1770, 970, 3600 |
| β-naphthyl | H | α-OH | D | LP | H0/Et$_2$O | 1770, 970, 3598 |
| β-naphthyl | H | β-OH | D | MP | | 1770, 970, 3598 |
| p-chlorophenyl | H | α-OH | D | LP | H0/Et$_2$O | 1770, 970, 3598 |
| p-chlorophenyl | H | β-OH | D | MP | | 1770, 970, 3598 |
| p-t-butylphenyl | H | α-OH | D | LP | H0/EtoAc | 1770, 970, 3598 |
| p-t-butylphenyl | H | β-OH | D | MP | | 1770, 970, 3598 |
| phenyl | (+)Me | α-OH | D | LP | 10%EtoAc/Benzene | 1770, 970, 3600 |
| phenyl | (+)Me | β-OH | D | MP | | 1770, 970, 3598 |
| phenyl | (−)Me | β-OH | D | LP | 20%Et$_2$O/Benzene | 1770, 970, 3600 |
| phenyl | (−)Me | β-OH | D | MP | | 1770, 970, 3600 |

$^{(a)}$D is trans double bond; S is single bond
$^{(b)}$TLC mobility LP=less polar, MP=more polar
$^{(c)}$Solvent system for column chromatography isomer separation

Additional Compounds

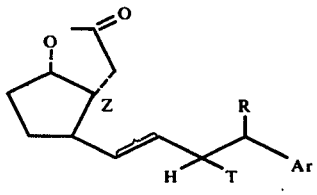

| Ar | T | R | Z* | IR data cm⁻¹ |
|---|---|---|---|---|
| m-methylphenyl | α-OTHP | H | D | 1770, 970 |
| m-methylphenyl | β-OTHP | H | D | 1770, 970 |
| o-biphenyl | α-OTHP | H | D | 1770, 970 |
| o-biphenyl | β-OTHP | H | D | 1770, 970 |
| 5-phenyl-2-thienyl | α-OTHP | H | D | 1770, 970 |
| 5-phenyl-2-thienyl | β-OTHP | H | D | 1770, 970 |
| β-naphthyl | α-OTHP | H | D | 1770, 970 |
| β-naphthyl | β-OTHP | H | D | 1770, 970 |
| p-chlorophenyl | α-OTHP | H | D | 1770, 970 |
| p-chlorophenyl | β-OTHP | H | D | 1770, 970 |
| p-t-butylphenyl | α-OTHP | H | D | 1770, 970 |
| p-t-butylphenyl | β-OTHP | H | D | 1770, 970 |
| phenyl | α-OTHP | (+)Me | D | 1770, 970 |
| phenyl | β-OTHP | (+)Me | D | 1770, 970 |
| phenyl | β-OTHP | (−)Me | D | 1770, 970 |
| phenyl | β-OTHP | (−)Me | D | 1770, 970 |

*D is trans double bond; S is single bond.

Additional Compounds

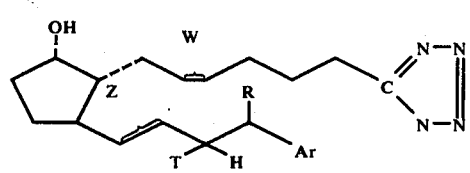

| Ar | T | R | W* | Z** |
|---|---|---|---|---|
| m-metylphenyl | α-OTHP | H | D | D |
| m-methylphenyl | β-OTHP | H | D | D |
| o-biphenyl | α-OTHP | H | D | D |
| o-biphenyl | β-OTHP | H | D | D |
| 5-phenyl-2-thienyl | α-OTHP | H | D | D |
| 5-phenyl-2-thienyl | β-OTHP | H | D | D |
| β-naphthyl | α-OTHP | H | D | D |
| β-naphthyl | β-OTHP | H | D | D |
| p-chlorophenyl | α-OTHP | H | D | D |
| p-chlorophenyl | β-OTHP | H | D | D |
| p-t-butylphenyl | α-OTHP | H | D | D |
| p-t-butylphenyl | β-OTHP | H | D | D |
| phenyl | α-OTHP | (+)Me | D | D |
| phenyl | β-OTHP | (+)Me | D | D |
| phenyl | α-OTHP | (−)Me | D | D |
| phenyl | β-OTHP | (−)Me | D | D |

*D is cis double bond; S is single bond.
**D is trans double bond; S is single bond.

Additional Compounds

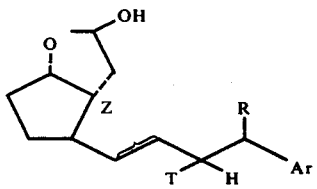

| Ar | T | R | Z* | IR data cm⁻¹ |
|---|---|---|---|---|
| m-methylphenyl | α-OTHP | H | D | 970 |
| m-methylphenyl | β-OTHP | H | D | 970 |
| o-biphenyl | α-OTHP | H | D | 970 |
| o-biphenyl | β-OTHP | H | D | 970 |
| 5-phenyl-2-thienyl | α-OTHP | H | D | 970 |
| 5-phenyl-2-thienyl | β-OTHP | H | D | 970 |
| β-naphthyl | α-OTHP | H | D | 970 |
| β-naphthyl | β-OTHP | H | D | 970 |
| p-chlorophenyl | α-OTHP | H | D | 970 |
| p-chlorophenyl | β-OTHP | H | D | 970 |
| p-t-butylphenyl | α-OTHP | H | D | 965 |
| p-t-butylphenyl | β-OTHP | H | D | 965 |
| phenyl | α-OTHP | (+)Me | D | 975 |
| phenyl | β-OTHP | (+)Me | D | 975 |
| phenyl | α-OTHP | (−)Me | D | 975 |
| pheyl | β-OTHP | (−)Me | D | 975 |

*D is trans double bond; S is single bond.

Additional Compounds

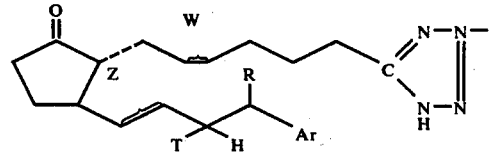

| Ar | T | R | W* | Z** | IR data |
|---|---|---|---|---|---|
| m-methylphenyl | α-OTHP | H | D | D | 1740, 970 |
| m-methylphenyl | β-OTHP | H | D | D | 1740, 970 |
| o-biphenyl | α-OTHP | H | D | D | 1740, 970 |
| o-biphenyl | β-OTHP | H | D | D | 1740, 970 |
| 5-phenyl-2-thienyl | α-OTHP | H | D | D | 1740, 970 |
| 5-phenyl-2-thienyl | β-OTHP | H | D | D | 1740, 970 |
| β-naphthyl | α-OTHP | H | D | D | 1738, 970 |
| β-naphthyl | β-OTHP | H | D | D | 1738, 970 |
| p-chlorophenyl | α-OTHP | H | D | D | 1740, 970 |
| p-chlorophenyl | β-OTHP | H | D | D | 1740, 970 |
| p-t-butylphenyl | α-OTHP | H | D | D | 1740, 965 |
| p-t-butylphenyl | β-OTHP | H | D | D | 1740, 965 |
| phenyl | α-OTHP | (+)Me | D | D | 1740, 970 |
| phenyl | β-OTHP | (+)Me | D | D | 1740, 970 |
| phenyl | α-OTHP | (−)Me | D | D | 1740, 970 |
| phenyl | β-OTHP | (−)Me | D | D | 1740, 970 |

*D is cis double bond; S is single bond.
**D is trans double bond; S is single bond.

Additional Compounds

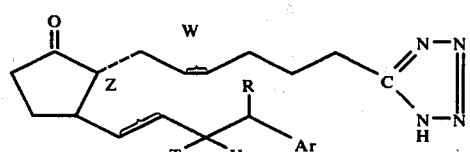

| Ar | T | R | W* | Z** | IR data cm⁻¹ |
|---|---|---|---|---|---|
| m-methylphenyl | α-OH | H | D | D | 3550 (broad) 1740, 970 |
| m-methylphenyl | β-OH | H | D | D | 3550 (broad) 1740, 970 |
| o-biphenyl | α-OH | H | D | D | 3550 (broad) 1740, 970 |
| o-biphenyl | β-OH | H | D | D | 3550 (broad) 1740, 970 |
| 5-phenyl-2-thienyl | α-OH | H | D | D | 3550 (broad) 1740, 970 |
| 5-phenyl-2-thienyl | β-OH | H | D | D | 3550 (broad) 1740, 970 |
| β-naphthyl | α-OH | H | D | D | 3550 (broad) 1740, 970 |
| β-naphthyl | β-OH | H | D | D | 3550 (broad) 1740, 970 |

Additional Compounds

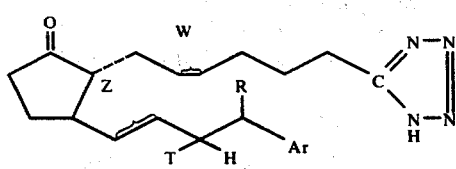

| Ar | T | R | W* | Z** | IR data cm⁻¹ |
|---|---|---|---|---|---|
| p-chlorophenyl | α-OH | H | D | D | 3550 (broad) 1740, 970 |
| p-chlorophenyl | β-OH | H | D | D | 3550 (broad) 1740, 970 |
| p-t-butylphenyl | α-OH | H | D | D | 3550 (broad) 1740, 965 |
| p-t-butylphenyl | β-OH | H | D | D | 3550 (broad) 1740, 965 |
| phenyl | α-OH | (+)Me | D | D | 3550 (broad) 1740, 970 |
| phenyl | β-OH | (+)Me | D | D | 3550 (broad) 1740, 970 |
| phenyl | α-OH | (−)Me | D | D | 3550 (broad) 1740, 970 |
| phenyl | β-OH | (−)Me | D | D | 3550 (broad) 1740, 970 |

*D is cis double bond; S is single bond.
**D is trans double bond; S is single bond.

Additional Compounds

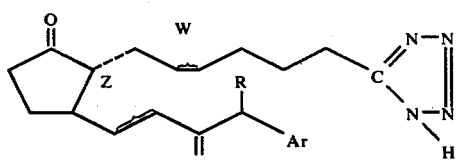

| Ar | R | W* | Z** | IR data cm⁻¹ |
|---|---|---|---|---|
| β-naphthyl | H | D | D | 1740, 1700, 1680, 1620, 970 |

*D is cis double bond; S is single bond.
**D is trans double bond; S is single bond.

EXAMPLE XL

To a solution, cooled to −78° in a dry nitrogen atmosphere, of 1.68g (4.40 mmole) of 2-descarboxy-2-(tetrazol-5-yl)-9,15-diketo-16-phenyl-ω-tetranor prostanoic acid in 25 ml of dry tetrahydrofuran was added dropwise 7.04 ml (3.52 mmole) of a 0.5 M solution of magnesium methoxide in methanol. After stirring at −78° for 5 min., the reaction mixture was allowed to warm to room temperature. The volatiles were removed by rotary evaporation and the resultant oil was triturated with ether to afford a white solid. The solid was washed thoroughly with ether and dried in vacuo to give 1.60g of magnesium salt.

The other magnesium salts of prostaglandin analogs of the present invention of the E and F series are prepared according to the above procedure.

Salts prepared by method of Example XL:

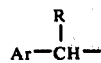

| | N | W | Z | Ar | R |
|---|---|---|---|---|---|
| | 0 | single bond | single bond | phenyl | H |
| racemic | 0 | single bond | single bond | phenyl | H |
| ent-stereochem | 0 | single bond | single bond | phenyl | H |
| | 0 | double bond | double bond | m-tolyl | H |
| | 0 | double bond | single bond | m-tolyl | H |

Salts prepared by method of Example XL:

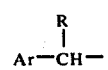

| N | W | Z | Ar | R |
|---|---|---|---|---|
| 0 | bond single bond | bond single bond | m-tolyl | H |
| 0 | single bond | single bond | p-tolyl | H |
| H, α-OH | single bond | single bond | phenyl | H |
| H, α-OH | double bond | double bond | phenyl | Me |
| H, α-OH | single bond | single bond | phenyl | Me |
| H, α-OH | double bond | double bond | p-biphenyl | H |

The melting point of all of the salts was greater than 250° C. with decomposition.

What is claimed is:

1. Magnesium salts of 2-descarboxy-2-[tetrazol-5-yl]-11-desoxy-ω-pentanorprostaglandins and their $C_{15}$ epimers having at the 15-position a hydroxy or a keto group and one substituent of the formula:

$$\overset{R}{\underset{|}{Ar-CH-}}$$

wherein Ar is α- or β-thienyl; 5-phenyl-α- or β-thienyl; 5-lower alkyl-α- or β-thienyl; α- or β-naphthyl; tropyl, phenyl; 3,5-dimethylphenyl; 3,4-dimethoxyphenyl; 3,4-methylenedioxyphenyl; 3,4-dichlorophenyl; and monosubstituted phenyl wherein said substituent is bromo, chloro, fluoro, trifluoromethyl, phenyl, lower alkyl, or lower alkoxy; and R is hydrogen or methyl.

2. Magnesium salts of 2-descarboxy-2-[tetrazol-5-yl]-11-desoxy-ω-pentanorprostaglandins of the E or F series and their $C_{15}$ epimers having at the 15-position a hydroxy or keto group and one substituent of the formula:

$$\overset{R}{\underset{|}{Ar-CH-}}$$

wherein Ar is α- or β-thienyl; 5-phenyl-α- or β-thienyl; 5-lower alkyl-α- or β-thienyl; α- or β-naphthyl; tropyl, phenyl; 3,5-dimethylphenyl; 3,4-dimethoxyphenyl; 3,4-methylenedioxyphenyl; 3,4-dichlorophenyl and monosubstituted phenyl wherein said substituent is bromo, chloro, fluoro, trifluoromethyl, phenyl, lower alkyl, or lower alkoxy; and R is hydrogen or methyl.

3. A magnesium salt of a compound of the structure:

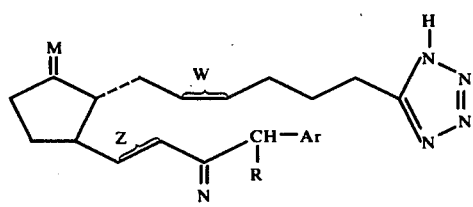

wherein Ar is α- or β-thienyl; 5-phenyl-α- or β-thienyl; 5-lower alkyl-α- or β-thienyl; α- or β-naphthyl; tropyl, phenyl; 3,5-dimethylphenyl, 3,4-dimethoxyphenyl; 3,4-methylenedioxyphenyl; 3,4-dichlorophenyl; and monosubstituted phenyl wherein said substituent is bromo, chloro, fluoro, trifluoromethyl, phenyl, lower alkyl, or lower alkoxy; R is hydrogen or methyl:
W is a single bond or cis double bond;
Z is a single bond or trans double bond; and
M and N are each keto,

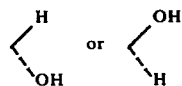

4. A magnesium salt of a compound of the structure:

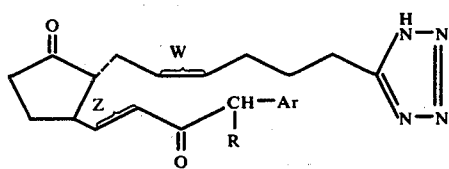

wherein Ar is α- or β-thienyl; 5-phenyl-α- or β-thienyl; 5-lower alkyl-α- or β-thienyl; α- or β-naphthyl; tropyl, phenyl; 3,5-dimethylphenyl; 3,4-dimethoxyphenyl; 3,4-methylenedioxyphenyl 3,4-dichlorophenyl; and monosubstituted phenyl wherein said substituent is bromo, chloro, fluoro, trifluoromethyl, phenyl, lower alkyl, or lower alkoxy; R is hydrogen or methyl;
W is a single bond or cis double bond; and
Z is a single bond or trans double bond.

5. A magnesium salt of a compound of the structure:

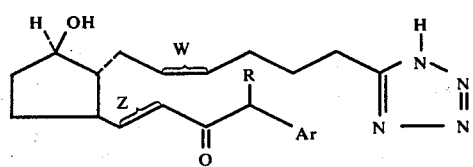

wherein Ar is α- or β-thienyl; 5-lower alkyl-α- or β-thienyl; α- or β-napthyl; tropyl, phenyl; 3,5-dimethylphenyl; 3,4-dimethyoxyphenyl; 3,4-methylenedioxyphenyl; 3,4-dichlorophenyl; and monosubstituted phenyl wherein said substituent is bromo, chloro, fluoro, trifluoromethyl, phenyl, lower alkyl, or lower alkoxy; R is hydrogen or methyl;
W is a single bond or cis double bond; and
Z is a single bond or trans double bond.

6. A magnesium salt of a compound of the formula:

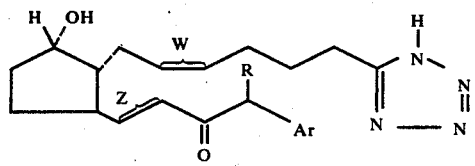

wherein Ar is α- or β-thienyl; 5-phenyl-α- or β-thienyl; 5-lower alkyl-α- or β-thienyl; α- or β-naphthyl; tropyl, phenyl 3,5-dimethylphenyl; 3,4-dimethoxyphenyl; 3,4-methylenedioxyphenyl; 3,4-dichlorophenyl; and monosubstituted phenyl wherein said substituent is bromo, chloro, fluoro, trifluoromethyl, phenyl, lower alkyl, or lower alkoxy; R is hydrogen or methyl;
W is a single bond or cis double bond; and
Z is a single bond or trans double bond.

7. A magnesium salt of a compound of the structure:

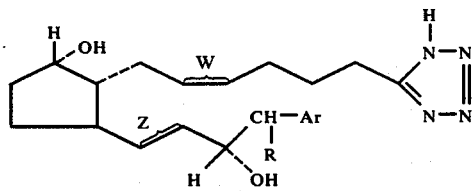

and the $C_{15}$ epimers thereof,
wherein Ar is α- or β-thienyl; 5-phenyl-α- or β-thienyl; 5-lower alkyl-α- or β-thienyl; α- or β-naphthyl; tropyl, phenyl; 3,5-dimethylphenyl; 3,4-dimethoxyphenyl; 3,4-methylenedioxyphenyl; 3,4-dichlorophenyl; and monosubstituted phenyl wherein said substituent is bromo, chloro, fluoro, trifluoromethyl, phenyl, lower alkyl, or lower alkoxy; R is hydrogen or methyl;
W is a single bond or cis double bond; and
Z is a single bond or trans double bond.

8. A magnesium salt of a compound of the structure:

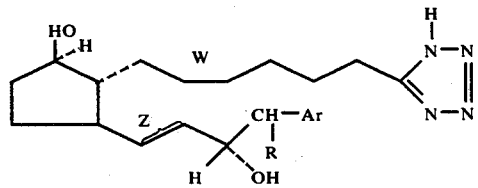

and the $C_{15}$ epimers thereof,
wherein Ar is α- or β-thienyl; 5-phenyl-α- or β-thienyl; 5-lower alkyl-α- or β-thienyl; α- or β-naphthyl; tropyl, phenyl; 3,5-dimethylphenyl; 3,4-dimethoxyphenyl; 3,4-methylenedioxyphenyl; 3,4-dichlorophenyl; and monosubstituted phenyl wherein said substituent is bromo, chloro, fluoro, trifluoromethyl, phenyl, lower alkyl, or lower alkoxy; R is hydrogen or methyl;
W is a single bond or cis double bond; and
Z is a single bond or trans double bond.

9. A magnesium salt of a compound of the structure:

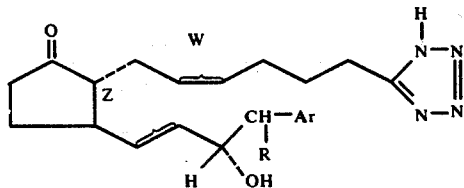

and the $C_{15}$ epimers thereof, wherein Ar is α- or β-thienyl; 5-phenyl-α- or β-thienyl; 5-lower alkyl-α- or β-thienyl; α- or β-naphthyl; tropyl, phenyl; 3,5-dimethylphenyl; 3,4-dimethoxyphenyl; 3,4-methylenedioxyphenyl; 3,4-dichlorophenyl; and monosubstituted phenyl wherein said substituent is bromo, chloro, fluoro, trifluoromethyl, phenyl, lower alkyl, or lower alkoxy; R is hydrogen or methyl;

W is a single bond or cis double bond; and

Z is a single bond or trans double bond.

10. A compound of claim 3 wherein W is a cis double bond and Z is a trans double bond.

11. A compound of claim 3 wherein W is a cis double bond and Z is a single bond.

12. A compound of claim 3 wherein both W and Z are single bonds.

13. A compound of claim 3 wherein W is a single bond and Z is a trans double bond.

14. A compound of claim 4 wherein W is a cis double bond and Z is a trans double bond.

15. A compound of claim 4 wherein W is a cis double bond and Z is a single bond.

16. A compound of claim 4 wherein W is a single bond and Z is a trans double bond.

17. A compound of claim 4 wherein both W and Z are single bonds.

18. A compound of claim 9 wherein W is a cis double bond and Z is a trans double bond.

19. A compound of claim 9 wherein both W and Z are single bonds.

20. A compound of claim 9 wherein W is a cis double bond and Z is a single bond.

21. A compound of claim 9 wherein W is a single bond and Z is a trans double bond.

22. A compound of claim 4 wherein Ar is m-tolyl, W is a cis double bond, Z is a trans double bond, and R is hydrogen.

23. A compound of claim 9 wherein Ar is phenyl, W is a cis double bond, Z is a trans double bond, and R is methyl.

24. A racemic compound of claim 4 wherein Ar is phenyl, W and Z are single bonds, and R is hydrogen.

25. A compound of claim 4 wherein Ar is m-tolyl, Z is a single bond, W is a cis double bond, and R is hydrogen.

26. A compound of claim 4 wherein Ar is m-tolyl, W is a single bond, Z is a single bond, and R is hydrogen.

27. A compound of claim 9 wherein Ar is phenyl, W and Z are single bonds, and R is methyl.

28. A compound of claim 4 wherein Ar is p-tolyl, W is a single bond, Z is a single bond, and R is hydrogen.

29. A compound of claim 9 wherein Ar is phenyl, W and Z are single bonds, and R is hydrogen.

30. A compound of claim 9 wherein Ar is p-bisphenyl, W is a cis double bond, Z is a trans double bond, and R is hydrogen.

31. The magnesium salt of an optically active compound of the structure:

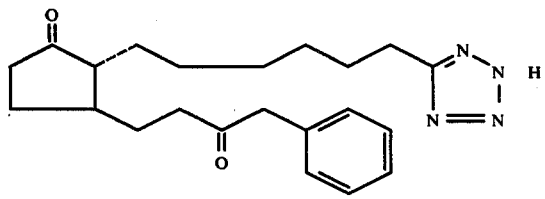

32. The magnesium salt of an optically active compound of the structure:

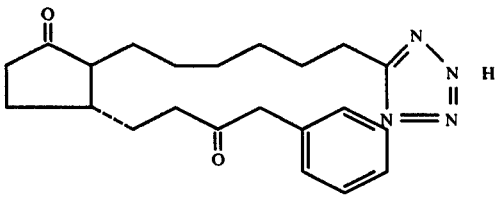

* * * * *

// UNITED STATES PATENT AND TRADEMARK OFFICE
CERTIFICATE OF CORRECTION

PATENT NO. : 4,035,360
DATED : July 12, 1977
INVENTOR(S) : Johnson et al

It is certified that error appears in the above-identified patent and that said Letters Patent are hereby corrected as shown below:

Col. 4, line 30, "∩" should read -- ω- --; line 31, "∩" should read -- ω --; line 32, "15" and "16" should read -- 15- -- and -- 16- --; line 33, "2" (first occurrence) should read -- 2- --; line 33, "∩" should read --ω- --; line 34, "15" should read -- 15- --; line 34, "descarboxy" should read -- descarboxy- --; line 45, "+" should read -- +) --; line 45, "methyl" should read -- methyl)- --; line 45, "16" (second occurrence) should read -- 16- --; line 46, "∩" should read -- ω --.

Col. 7, second formula under Scheme B, label the same -- <u>10</u> --.

Col. 8, first formula under Scheme B (formula marked 12) that portion of the formula reading "  "        should read   --  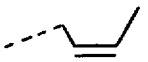   --;

UNITED STATES PATENT AND TRADEMARK OFFICE
CERTIFICATE OF CORRECTION

PATENT NO. : 4,035,360
DATED : July 12, 1977
INVENTOR(S) : Johnson et al

It is certified that error appears in the above-identified patent and that said Letters Patent are hereby corrected as shown below:

second formula under Scheme B, label the same -- 13 --; second formula under Scheme B, that portion of the formula reading "  "   should read  --    --.

Columns 7 and 8, insert -- 15 -- under the arrow extending downwardly from formula 12 to the end of the page.

Col. 9, second formula, label the same -- 15 --; left hand formula under Scheme C, label the same -- 16 --.

Columns 9 and 10, under Scheme B, delete the downwardly extending arrow.

Col. 10, right hand formula under Scheme C, label the same -- 6 --.

UNITED STATES PATENT AND TRADEMARK OFFICE
CERTIFICATE OF CORRECTION

PATENT NO. : 4,035,360
DATED : July 12, 1977
INVENTOR(S) : Johnson et al

It is certified that error appears in the above-identified patent and that said Letters Patent are hereby corrected as shown below:

Columns 13 and 14, insert -- ⟶ -- between structural formulas 25 and 26 under Scheme E; insert -- ⟶ -- between structural formulas 27 and 28 under Scheme E; insert -- ⟶ -- between structural formulas 29 and 30 under Scheme E; insert -- ⟶ -- between structural formulas 31 and 32 under Scheme E.

Col. 15, first structural formula, that portion of the formula reading

" 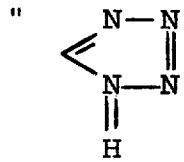 "   should read -- 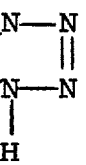 --;

second structural formula under Scheme F, that portion of the formula reading

" 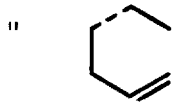 "   should read --  --;

UNITED STATES PATENT AND TRADEMARK OFFICE
CERTIFICATE OF CORRECTION

PATENT NO. : 4,035,360
DATED : July 12, 1977
INVENTOR(S) : Johnson et al

It is certified that error appears in the above-identified patent and that said Letters Patent are hereby corrected as shown below:

second structural formula under Scheme F, that portion of the formula reading

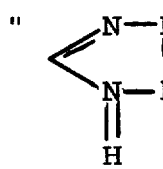   should read   -- 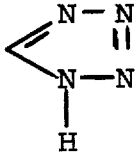 --;

third structural formula, that portion of the formula reading

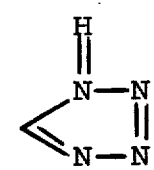   should read   -- 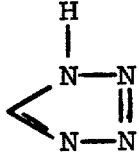 --;

fourth structural formula, that portion of the formula reading

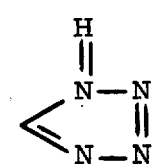   should read   -- 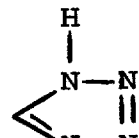 --.

UNITED STATES PATENT AND TRADEMARK OFFICE
CERTIFICATE OF CORRECTION

PATENT NO. : 4,035,360
DATED : July 12, 1977
INVENTOR(S) : Johnson et al

It is certified that error appears in the above-identified patent and that said Letters Patent are hereby corrected as shown below:

Col. 16, first structural formula, that portion of the formula reading

" 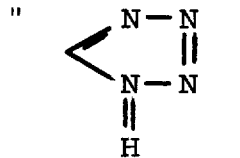 "   should read   -- 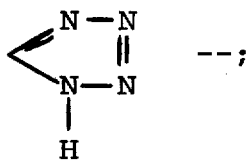 --;

second structural formula, that portion of the formula reading

" 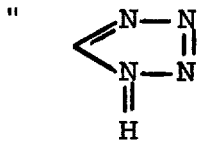 "   should read   -- 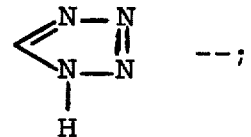 --;

third structural formula, that portion of the formula reading

" 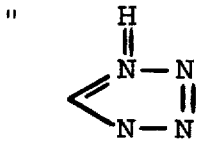 "   should read   -- 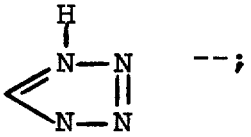 --;

Page 6 of 7

UNITED STATES PATENT AND TRADEMARK OFFICE
CERTIFICATE OF CORRECTION

PATENT NO. : 4,035,360
DATED : July 12, 1977
INVENTOR(S) : Johnson et al

It is certified that error appears in the above-identified patent and that said Letters Patent are hereby corrected as shown below:

fourth structural formula, that portion of the formula reading

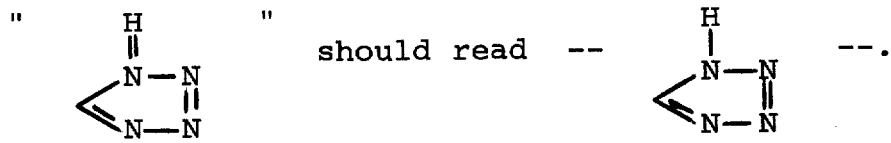

Col. 36, line 5, that portion of the formula reading

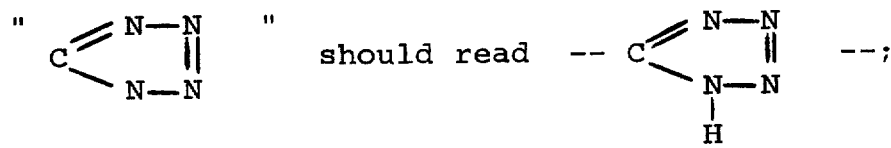

line 10, first entry in the table should read -- m-methylphenyl --; line 30, that portion of the formula reading "N-N-" should read -- N-N --.

Col. 38, line 25, that portion of the formula reading

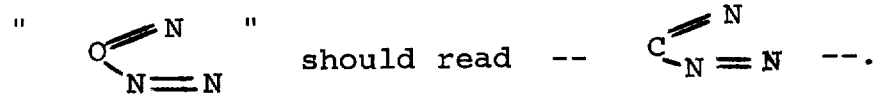

UNITED STATES PATENT AND TRADEMARK OFFICE
CERTIFICATE OF CORRECTION

PATENT NO. : 4,035,360
DATED : July 12, 1977
INVENTOR(S) : Johnson et al

It is certified that error appears in the above-identified patent and that said Letters Patent are hereby corrected as shown below:

Claim 8, line 2, that portion of the formula reading

"  " should read -- 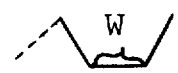 --.

Claim 32, line 3, that portion of the formula reading

" $\begin{matrix} N & H \\ \| & \\ N & \end{matrix}$ " should read -- $\begin{matrix} N\text{---}H \\ | \\ N \end{matrix}$ --.

Signed and Sealed this

Eleventh Day of April 1978

[SEAL]

Attest:

RUTH C. MASON
Attesting Officer

LUTRELLE F. PARKER
Acting Commissioner of Patents and Trademarks